US012703758B2

(12) United States Patent
Liu et al.

(10) Patent No.: US 12,703,758 B2
(45) Date of Patent: Aug. 11, 2026

(54) ANTI-CD3E/BCMA BISPECIFIC ANTIBODY AND USE THEREOF

(71) Applicant: Chongqing Genrix Biopharmaceutical Co., Ltd., Chongqing (CN)

(72) Inventors: Zhigang Liu, Beijing (CN); Shunan Wan, Beijing (CN); Yulan Liu, Beijing (CN); Xiaobo Hao, Beijing (CN); Junjie Hu, Beijing (CN); Jingjing Guo, Beijing (CN)

(73) Assignee: CHANGQING GENRIX BIOPHARMACEUTICAL CO., LTD., Chongqing (CN)

( * ) Notice: Subject to any disclaimer, the term of this patent is extended or adjusted under 35 U.S.C. 154(b) by 0 days.

(21) Appl. No.: 19/225,370

(22) Filed: Jun. 2, 2025

(65) Prior Publication Data

US 2025/0289901 A1 Sep. 18, 2025

Related U.S. Application Data

(63) Continuation-in-part of application No. 17/620,290, filed as application No. PCT/CN2019/102817 on Aug. 27, 2019, now Pat. No. 12,497,455.

(30) Foreign Application Priority Data

Jun. 19, 2019 (CN) ........................ 201910532734.7

(51) Int. Cl.
*C07K 16/28* (2006.01)
*A61K 39/00* (2006.01)
*A61P 35/00* (2006.01)

(52) U.S. Cl.
CPC .......... *C07K 16/2878* (2013.01); *A61P 35/00* (2018.01); *C07K 16/2809* (2013.01); *A61K 2039/505* (2013.01); *C07K 2317/24* (2013.01); *C07K 2317/31* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 9,273,141 | B2 | 3/2016 | Algate et al. |
| 10,253,104 | B2 | 4/2019 | Vu et al. |
| 2013/0058936 | A1 | 3/2013 | Bruenker et al. |
| 2013/0156769 | A1 | 6/2013 | Kufer et al. |
| 2017/0051068 | A1 | 2/2017 | Pillarisetti et al. |
| 2017/0327571 | A1 | 11/2017 | Liu et al. |
| 2017/0327579 | A1 | 11/2017 | Vu et al. |
| 2018/0022807 | A1 | 1/2018 | Katsurirangan et al. |
| 2020/0062853 | A1 | 2/2020 | Altintas et al. |

FOREIGN PATENT DOCUMENTS

| | | | |
|---|---|---|---|
| CN | 105315371 | A | 2/2016 |
| CN | 106831995 | A | 6/2017 |
| CN | 106831996 | A | 6/2017 |
| CN | 107428839 | A | 12/2017 |
| CN | 109152835 | A | 1/2019 |
| CN | 109641959 | A | 4/2019 |
| CN | 110229232 | B | 5/2019 |
| CN | 110172100 | A | 8/2019 |
| CN | 110229232 | A | 9/2019 |
| EA | 28162 | B1 | 10/2017 |
| EP | 2982692 | A1 | 2/2016 |
| RU | 2605390 | C2 | 12/2016 |
| WO | 2013/026839 | A1 | 2/2013 |
| WO | 2016/079081 | A1 | 5/2016 |
| WO | 2016/079177 | A1 | 5/2016 |
| WO | 2016/087531 | A1 | 6/2016 |
| WO | 2017/021450 | A1 | 2/2017 |
| WO | 2018/176992 | A1 | 10/2018 |

OTHER PUBLICATIONS

Acceptance Decision in related Russian Patent Application No. 2022100401/10(000718), dated Jun. 1, 2023, in Russian with English translation (11 pages).
Al-Lazikani et al., "Standard Conformations for the Canonical Structures of Immunoglobulins", J. Mol. Biol., Aug. 1997, vol. 273, Issue 4, pp. 927-948.
Canfield et al., "The Binding Affinity of Human IgG for its High Affinity Fc Receptor is Determined by Multiple Amino Acids in the CH2 Domain and is Modulated by the Hinge Region"; J. Exp. Med., Jun. 1, 1991, vol. 173, Issue 6, pp. 1483-1491.
Cho et al., "Targeting B Cell Maturation Antigen (BCMA) in Multiple Myeloma: Potential Uses of BCMA-Based Immunotherapy", Frontiers in Immunology, Aug. 10, 2018, vol. 9, Article 1821, pp. 1-15.
Coquery et al., "Regulatory Roles of the Tumor Necrosis Factor Receptor BCMA", Crit. Rev. Immunol., 2012, vol. 32, No. 4, pp. 287-305.
European Patent Office, Extended European Search Report in related European Patent Application No. 19934266.8 dated Jul. 11, 2023 (15 pages).
Gavriatopoulou et al., "Anti-BCMA antibodies in the future management of multiple myeloma", Expert Review of Anticancer Therapy, Feb. 27, 2019, vol. 19, Issue 4, pp. 319-326.
International Search Report and Written Opinion of International Searching Authority for International Application No. PCT/CN2019/102817, mailed Mar. 19, 2020 (22 pages).
Kabat et al., "Sequences of Proteins of Immunological Interest", vol. I, Fifth Edition; U.S. Department of Health and Human Services, National Institutes of Health, Bethesda, Md., 1991 (1251 pages).
Letouze et al., "Mechanisms of resistance to bispecific T-cell engagers in multiple myeloma and their clinical implications", Blood Adv., Mar. 26, 2024, vol. 8, Issue 11, pp. 2952-2959.

(Continued)

*Primary Examiner* — Misook Yu
*Assistant Examiner* — Samantha Lake Hopkins
(74) *Attorney, Agent, or Firm* — Lathrop GPM LLP; Malaika O.D. Tyson

(57) ABSTRACT

A bispecific antibody, which comprises an antigen-binding portion against human CD3E and/or an antigen-binding portion against human BCMA. Additionally, provided are medical and biological uses of the bispecific antibody.

1 Claim, 5 Drawing Sheets

Specification includes a Sequence Listing.

(56) References Cited

OTHER PUBLICATIONS

Liu et al., "Fc Engineering for Developing Therapeutic Bispecific Antibodies and Novel Scaffolds", Frontiers in Immunology, Jan. 2017, vol. 8, Article 38, pp. 1-15.
Mandikian et al., "Relative Target Affinities of T-Cell-Dependent Bispecific Antibodies Determine Biodistribution in a 'Solid Tumor Mouse Model", Mol. Cancer Ther., Apr. 2018, vol. 17, Issue 4, pp. 776-785.
Mariuzza et al., "The Structural Basis of Antigen-Antibody Recognition"; Ann. Rev. Biophys. Chem., 1987, vol. 16, pp. 139-159.
Martin et al., "Modeling antibody hypervariable loops: A combined algorithm", Proc. Natl. Acad. Sci. USA, Dec. 1989, vol. 86, pp. 9268-9272.
Mayo Clinic, "Cancer Treatment", Jul. 26, 2024. (7 pages) Retrieved from url: <https://www.mayoclinic.org/tests-procedures/cancer-treatment/about/pac-20393344>.
Merchant et al., "An efficient route to human bispecific IgG", Nature Biotechnology, Jun. 4, 1998, vol. 16, pp. 677-681.
Muller et al., "Spliceosomal peptide P140 for immunotherapy of systemic lupus erythematosus: Results of an early phase II clinical trial"; Arthritis & Rheumatism, Dec. 2008, vol. 58, No. 12, pp. 3873-3883.
NCFR, "Cancer Intervention vs. Prevention: What Does It Mean?", May 14, 2024. (2 pages). Retrieved from url: <https://www.nfcr.org/blog/cancer-intervention-vs-prevention-what-does-it-mean/>.
NIH-NCI, "Cancer Prevention Overview (PDQ®)—Patient Version", Oct. 23, 2023, (13 pages). Retrieved from url: <https://www.cancer.gov/about-cancer/causes-prevention/patient-prevention-overview-pdq>.
Office Action in related Russian Patent Application No. 2022100401/10(000718), dated Jan. 23, 2023, in Russian, with English translation. (17 pages).
Roitt et al., "Immunology", Fifth Edition, Moskva, Mir., pp. 110-111; C.V. Mosby Co., copyright 1998, in Russian with English-language summary; ISBN10: 0723429189 (5 pages).
Seckinger et al., "Target Expression, Generation, Preclinical Activity, and Pharmacokinetics of the BCMA-T Cell Bispecific Antibody EM801 for Multiple Myeloma Treatment", Cancer Cell, Mar. 2, 2017, vol. 31, pp. 396-410.
Shiraiwa et al.; "Engineering a bispecific antibody with a common light chain: Identification and optimization of an anti-CD3 epsilon and anti-GPC3 bispecific antibody, ERY974", Methods, Feb. 1, 2019, vol. 154, pp. 10-20.
Singer et al., "Genes & Genomes: A Changing Perspective", Moskva, Mir, v. 1, pp. 63-64, copyright 1998, in Russian with English-language summary. (5 pages).
Van Blarcom et al., "Productive common light chain libraries yield diverse panels of high affinity bispecific antibodies", mAbs, Feb. 17, 2018, vol. 10, No. 2, pp. 256-268.
Xiong et al., "A Novel CD3/BCMA Bispecific T-cell Redirecting Antibody for the Treatment of Multiple Myeloma", J. Immunother., Feb.-Mar. 2022, vol. 45, Issue 2, pp. 78-88.
Zuch De Zafra et al., "Targeting Multiple Myeloma with AMG 424, a Novel Anti-CD38/CD3 Bispecific T-cell-recruiting Antibody Optimized for Cytotoxicity and Cytokine Release"; Clin. Cancer Res., Mar. 27, 2019, vol. 25, No. 13, pp. 3921-3933.

ANTI-CD3E/BCMA BISPECIFIC ANTIBODY AND USE THEREOF

CROSS REFERENCE TO RELATED APPLICATIONS

The present application is a continuation in part of U.S. application Ser. No. 17/620,290, which is a U.S. National Stage of International Application Patent No. PCT/CN2019/102817, filed on Aug. 27, 2019, which claims the benefit of and priority to Chinese Patent Application No. 201910532734.7, filed on Jun. 19, 2019, both of which are incorporated herein by reference in their respective entireties.

INCORPORATION BY REFERENCE OF AN ELECTRONIC SEQUENCE LISTING

This application contains a sequence listing that has been submitted in a computer readable format and is hereby incorporated by reference in its entirety. The computer readable file, created on Jun. 2, 2025, is named CULT-934USCIP.xml and is 44,523 bytes in size.

TECHNICAL FIELD

The present application generally relates to the field of antibody drugs. In particular, the present application relates to a bispecific antibody comprising an antigen-binding portion against human CD3E and/or an antigen-binding portion against human BCMA and medical and biological uses thereof.

BACKGROUND

Bispecific antibody (BsAb) is a type of artificial antibody that comprises two different antigen binding sites. Bispecific antibodies are widely used in the field of biomedicine, especially tumor immunotherapy. One arm of the bispecific antibodies targeting CD3 can bind to the CD3E subunit in TCR receptor complex on the surface of T cells to provide a first signal to activate T cells, and the other arm targets tumor antigen. Bispecific antibodies can bring tumor cells and T cells closer together, and directly kill tumor cells while activating T cells.

There are numerous platforms for bispecific antibodies and their structures are complex. In terms of antibody structures, bispecific antibodies can be divided into two categories: those with Fc segments and those without Fc segments. The bispecific antibodies without Fc segments consist of the VH and VL regions or Fab fragments from two antibodies. The main representatives of such bispecific antibodies are BiTE, DART, TandAbs, bi-nanobody, and the like. The advantage of such bispecific antibodies is that there is no mismatch between heavy and light chains, and the disadvantage is that the half-life is short and the clinical application is inconvenient. The bispecific antibodies with Fc segments retain the structures of conventional monoclonal antibodies and can mediate the biological function of the Fc segments. The representatives of such bispecific antibodies are KIH IgQ crossmab, DVD-Ig, Triomab, and the like, which have a long half-life in vivo and can have ADCC and CDC activities (Hongyan Liu, Abhishek Saxena, Sachdev S. Sidhu, et al., Fc engineering for Developing Therapeutic Bispecifc Antibodies and Novel Scaffolds. *Front. Immunol.* 2017; 8:38).

Therefore, in view of the wide applicability of bispecific antibodies, there is a need to develop new bispecific antibodies in the art.

SUMMARY OF THE INVENTION

In a first aspect, there is provided in the present application a bispecific antibody comprising an antigen-binding portion against human CD3E, wherein the antigen-binding portion against human CD3E comprises:

HCDR1 (heavy chain CDR1) as set forth in SEQ ID NO:1,
HCDR2 (heavy chain CDR2) as set forth in SEQ ID NO:2,
HCDR3 (heavy chain CDR3) as set forth in SEQ ID NO:3,
LCDR1 (light chain CDR1) as set forth in SEQ ID NO:4,
LCDR2 (light chain CDR2) as set forth in SEQ ID NO:5, and
LCDR3 (light chain CDR3) as set forth in SEQ ID NO:6;
wherein HCDRs and LCDRs are defined according to Kabat.

In a second aspect, there is provided in the present application a bispecific antibody comprising an antigen-binding portion against human BCMA, wherein the antigen-binding portion against human BCMA comprises:

HCDR1 (heavy chain CDR1) as set forth in SEQ ID NO:7,
HCDR2 (heavy chain CDR2) as set forth in SEQ ID NO:8,
HCDR3 (heavy chain CDR3) as set forth in SEQ ID NO:9,
LCDR1 (light chain CDR1) as set forth in SEQ ID NO:4,
LCDR2 (light chain CDR2) as set forth in SEQ ID NO:5, and
LCDR3 (light chain CDR3) as set forth in SEQ ID NO:6;
wherein HCDRs and LCDRs are defined according to Kabat.

In a third aspect, there is provided in the present application a bispecific antibody comprising an antigen-binding portion against human CD3E and an antigen-binding portion against human BCMA.

In some embodiments of the third aspect, the antigen-binding portion against human CD3E comprises:

HCDR1 as set forth in SEQ ID NO:1,
HCDR2 as set forth in SEQ ID NO:2,
HCDR3 as set forth in SEQ ID NO:3,
LCDR1 as set forth in SEQ ID NO:4,
LCDR2 as set forth in SEQ ID NO:5, and
LCDR3 as set forth in SEQ ID NO:6;
wherein HCDRs and LCDRs are defined according to Kabat.

In some embodiments of the third aspect, the antigen-binding portion against human BCMA comprises:

HCDR1 as set forth in SEQ ID NO:7,
HCDR2 as set forth in SEQ ID NO:8,
HCDR3 as set forth in SEQ ID NO:9,
LCDR1 as set forth in SEQ ID NO:4,
LCDR2 as set forth in SEQ ID NO:5, and
LCDR3 as set forth in SEQ ID NO:6;
wherein HCDRs and LCDRs are defined according to Kabat.

In some embodiments of the third aspect, the antigen-binding portion against human CD3E and the antigen-binding portion against human BCMA comprise the same light chain variable region.

In some embodiments of the third aspect, the bispecific antibody is an IgG1 antibody comprising two heavy chain constant regions having the same hinge region, and the amino acid sequence of the hinge region is shown in SEQ ID NO:15.

In some embodiments of the third aspect, the bispecific antibody is an IgG1 antibody comprising a first heavy chain constant region and a second heavy chain constant region, wherein the amino acids at positions 354 and 366 of the first heavy chain constant region are C and W, respectively, and the amino acids at positions 349, 366, 368 and 407 of the second heavy chain constant region are C, S, A and V, respectively; the amino acid position of the antibody constant region is determined according to EU numbering.

In some embodiments of the third aspect, the bispecific antibody is an IgG1 antibody comprising a first heavy chain constant region and a second heavy chain constant region, wherein the amino acids at positions 234, 235 and 331 of the first and second heavy chain constant regions are F, E, and S, respectively; the amino acid position of the antibody constant region is determined according to EU numbering.

In some embodiments of the first and third aspects, the antigen-binding portion against human CD3E comprises a heavy chain variable region as set forth in SEQ ID NO: 12 and a light chain variable region as set forth in SEQ ID NO: 14.

In some embodiments of the second and third aspects, the antigen-binding portion against human BCMA comprises a heavy chain variable region as set forth in SEQ ID NO: 10 and a light chain variable region as set forth in SEQ ID NO:14.

In some embodiments of any of the above aspects, the antigen-binding portion against human CD3E comprises a single chain antibody (scfv) or a Fab fragment.

In some embodiments of any of the above aspects, the antigen-binding portion against human BCMA comprises a single chain antibody (scfv) or a Fab fragment.

In some embodiments of the third aspect, the antibody has a first arm and a second arm, wherein the first arm comprises an antigen-binding portion against human CD3E and the second arm comprises an antigen-binding portion against human BCMA:

- the first arm comprises the amino acid sequence of the heavy chain variable region as set forth in SEQ ID NO:12, the amino acid sequence of the heavy chain constant region as set forth in SEQ ID NO:19, the amino acid sequence of the light chain variable region as set forth in SEQ ID NO: 14, and the amino acid sequence of the light chain constant region as set forth in SEQ ID NO: 20;
- the second arm comprises the amino acid sequence of the heavy chain variable region as set forth in SEQ ID NO: 10, the amino acid sequence of the heavy chain constant region as set forth in SEQ ID NO: 18, the amino acid sequence of the light chain variable region as set forth in SEQ ID NO: 14, and the amino acid sequence of the light chain constant region as set forth in SEQ ID NO:20.

In some embodiments of third aspect, the antibody has a first arm and a second arm, wherein the first arm comprises an antigen-binding portion against human CD3E, wherein the first arm comprises a heavy chain variable region comprising the amino acid sequence of SEQ ID NO: 12, a heavy chain constant region comprising the amino acid sequence of SEQ ID NO:37, a light chain variable region comprising the amino acid sequence of SEQ ID NO:14, and a light chain constant region comprising the amino acid sequence of SEQ ID NO:20, and the second arm comprises an antigen-binding portion against human BCMA, wherein the second arm comprises a heavy chain variable region comprising the amino acid sequence of SEQ ID NO:10, a heavy chain constant region comprising the amino acid sequence of SEQ ID NO:38, a light chain variable region comprising the amino acid sequence of SEQ ID NO:14, and a light chain constant region comprising the amino acid sequence of SEQ ID NO:20.

In some embodiments of third aspect, the antibody has the first arm comprises the amino acid sequences of SEQ ID NOs: 39 and 41 and the second arm comprises the amino acid sequences of SEQ ID NOs: 40 and 41

In a fourth aspect, there is provided in the present application a pharmaceutical composition comprising the bispecific antibody of any one of the first to third aspects.

In a fifth aspect, there is provided in the present application use of the bispecific antibody of any one of the first to third aspects or the pharmaceutical composition of the fourth aspect in the manufacture of a medicament for the prevention or treatment of multiple myeloma.

In a sixth aspect, there is provided in the present application a method of preventing or treating multiple myeloma, comprising administering the bispecific antibody of any one of the first to third aspects or the pharmaceutical composition of the fourth aspect to a subject in need thereof.

DETAILED DESCRIPTION OF THE INVENTION

Definitions

Figure 1:
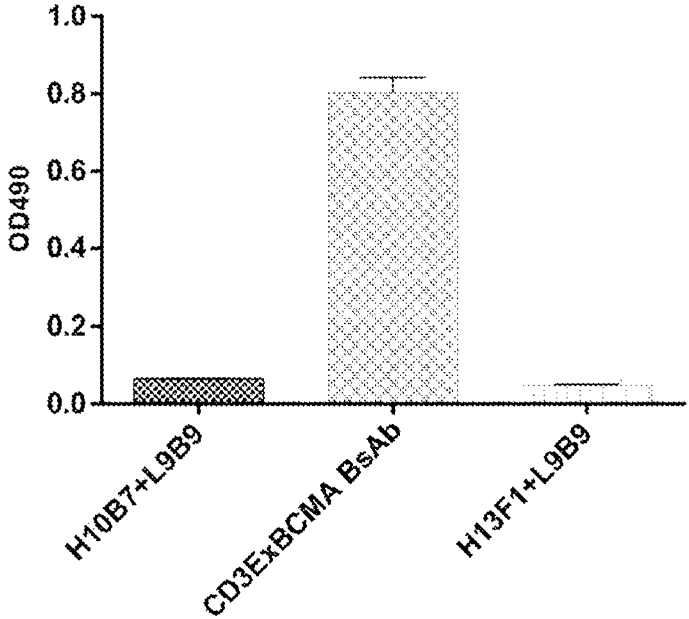
FIG. 1 shows the results of detecting the simultaneous binding of the bispecific antibody CD3ExBCMA to both CD3E and BCMA antigens by using the ELISA method.

The following definitions and methods are provided to better define the present application and guide those of ordinary skill in the art in the practice of the present application. Unless otherwise indicated, the terms used in the present application have the meanings commonly understood by those skilled in the art. All patent documents, academic papers, and other publications cited herein are incorporated by reference in their entirety.

When describing the structure of the antibody herein, reference is made to the EU numbering definition of human IgG1 antibody with respect to the description on amino acid position numbering, which is well known and readily available to those skilled in the art. Furthermore, where a mutation is described herein in connection with the EU numbering position, it refers to a mutation produced relative to the native antibody sequence.

As used herein, the term "Fc fragment", "Fc domain", "Fc portion" or the like refers to a portion of the heavy chain constant region of an antibody, including the hinge region, the CH2 segment and the CH3 segment of the constant region. With reference to the EU numbering definition of the human IgG1 antibody, the Fe fragment refers to the amino acid sequence at positions 216-447 in the constant region of the antibody.

As used herein, the term "Fab (fragment antigen-binding) fragment", "Fab portion", or the like refers to an antibody fragment capable of binding to an antigen that are produced after treatment of an intact antibody with papain, including the intact light chain (VL-CL), the heavy chain variable region, and the CH1 fragment (VH-CH1).

As used herein, the term "single chain fragment variable (scFv)" refers to an antibody of a single chain structure comprising a polypeptide chain comprising a heavy chain variable region (VH) and a light chain variable region (VL), which is generally constructed using genetic engineering techniques. A flexible linker is typically designed between the heavy chain variable region and the light chain variable region so that the heavy chain variable region and the light chain variable region can be folded into the correct conformation capable of binding to an antigen.

As used herein, the term "antigen-binding portion" refers to a portion of the antibody structure that determines the antigen-binding ability. It will be appreciated by those skilled in the art that the major parts of the antibody structure that determines the antigen-binding ability are the CDRs, so the CDRs are also the core components of the antigen-binding portion. In the construction of a bispecific antibody, the examples of the "antigen-binding portion" include, but are not limited to, a single chain antibody (scfv) or a Fab fragment.

As used herein, the term "bispecific antibody" refers to an antibody having the ability to bind to two different antigens, which may consist of two Fc fragments and two antigen-binding portions fused thereto, respectively.

In some embodiments, "bispecific antibody" used herein refers to a bispecific antibody based on human IgG1 antibody, and in addition to the altered structures described herein, it has the basic characteristics and function of human IgG1 antibody. It is well-known to those skilled in the art that "bispecific antibody" used herein may also be a bispecific antibody based on other immunoglobulin subtype, such as human IgG2 antibody.

It is well known to those skilled in the art that complementarity determining regions (CDRs, usually including CDR1, CDR2 and CDR3) are the regions of a variable region that have mostly impact on the affinity and specificity of an antibody. The CDR sequences of a VH or VL have two common definitions, i.e., the Kabat definition and the Chothia definition (see, e.g., Kabat, "Sequences of Proteins of Immunological Interest", National Institutes of Health, Bethesda, Md. (1991); Al-Lazikani et al., J. MOL Biol. 273:927-948 (1997); and Martin et al., Proc. Natl. Acad. Sci. USA, 86:9268-9272 (1989)). For the variable region sequences of a given antibody, the sequences of CDR regions in the VH and VL can be determined according to the Kabat definition or the Chothia definition. In some embodiments of the present application, CDR sequences are defined according to the Kabat definition.

For the variable region sequences of a given antibody, the sequences of CDR regions in the variable region sequences can be analyzed in a variety of ways, for example, using online software Abysis (www.abysis.org).

As used herein, the term "specific binding" refers to a non-random binding reaction between two molecules, e.g., binding of an antibody to an antigen epitope.

CD3 molecule is an important differentiation antigen on T cell membrane and is also a characteristic marker of mature T cells. CD3 molecule consists of four chains of γ, δ, ε, and ζ, or five chains of γ, δ, ε, ζ, and η (ζ, and η are homologous isomers), is composed of three dimers of CD3γε, CD3δε and CD3ζζ (or CD3ζη) and expressed on T cell membrane. Three chains of CD3γ, δ and ε contain highly conserved acidic amino acid residues (glutamic acid in γ chain, and aspartic acid in δ and ε chains), which can be non-covalently linked to the basic amino acid residues on the α and β chains of the T cell receptor (TCR) by a salt bridge to form a stable TCR-CD3 complex structure. The complex can transmit T cell activation signals and stabilize the TCR structure. The intracellular domain of each chain of CD3 contains an ITAM (immune receptor tyrosine-based activation motif) structure, which is the basis for CD3 molecule-mediated intracellular signaling. When the TCR specifically recognizes and binds to an antigen (an antigenic peptide presented by an MHC molecule), tyrosine protein kinases within T cells phosphorylate tyrosine residues on ITAM, and recruit tyrosine protein kinases containing SH2 domains (ZAP-70). The signal is transduced into the cytoplasm of T cells to initiate activation mechanism within the cells. Therefore, CD3 has the function of transmitting the activation signal generated after TCR recognizes the antigen and the signal is the first signal for inducing T cell activation.

B cell maturation antigen (BCMA) is the 17th member of the TNF receptor superfamily. As a non-glycosylated type III transmembrane protein receptor, BCMA consists of 184 amino acid residues with 80 amino acid residues in the intracellular region and only one carbohydrate recognition domain in the extracellular region. BCMA is involved in B cell maturation and differentiation as a specific antigen on the surface of plasma cells. BCMA is also involved in long-term survival of plasma cells as an essential substance. BCMA, TACI and BAFFR respectively bind to two ligands, i.e., a proliferation-inducing ligand (APRIL) and B cell activation factor (BAFF), and participate in activation of signal transduction molecules such as p38, Elk and c-Jun via the NFKB pathway, thereby affecting the maturation, growth and survival of B cells. However, BCMA is not critical for B-cell survival. It has been shown that the production of short-term immunoglobulin, the early humoral immune response and the development of B-lymphocyte in mouse plasma cells after BCMA knockout are not affected (Christine M. Coquery, Loren D. Erickson. Regulatory Roles of the Tumor Necrosis Factor Receptor BCMA. *Crit Rev Immunol.* 2012; 32 (4): 287-305). The expression of BCMA is selective. It is not expressed in naive B cells, memory B cells, CD34+ hematopoietic cells and other normal tissues, and is selectively induced to be expressed during differentiation of plasma cells, and is mainly expressed on plasma-like dendritic cells and bone marrow plasma cells. Multiple myeloma is a B cell malignant tumor caused by malignant proliferation and canceration of cells. It is mainly manifested by the uncontrolled expansion of plasma cells in the bone man ow and the production of a large number of monoclonal immunoglobulins, which result in a series of symptoms such as bone destruction, elevated blood calcium, anemia, renal damage, immune decline, and the like. The expression level of BCMA in myeloma cells is significantly higher than that in plasma cells and plasmablasts. BCMA is highly and widely expressed throughout the course of plasma cell malignant diseases including monoclonal gammopathy to smoldering myeloma, and further to multiple myeloma (Shih-Feng Cho, Kenneth C. Anderson, Yu-Tzu Tai. Targeting B Cell Maturation Antigen (BCMA) in Multiple Myeloma: Potential Uses of BCMA-Based immunotherapy. *Front. Immunol.*, 2018; 9:1821).

In a first aspect, there is provided in the present application a bispecific antibody comprising an antigen-binding portion against human CD3E, wherein the antigen-binding portion against human CD3E comprises:

HCDR1 as set forth in SEQ ID NO:1,
HCDR2 as set forth in SEQ ID NO:2,
HCDR3 as set forth in SEQ ID NO:3,
LCDR1 as set forth in SEQ ID NO:4,
LCDR2 as set forth in SEQ ID NO:5, and
LCDR3 as set forth in SEQ ID NO:6;
wherein HCDRs and LCDRs are defined according to Kabat.

In a second aspect, there is provided in the present application a bispecific antibody comprising an antigen-binding portion against human BCMA, wherein the antigen-binding portion against human BCMA comprises:

HCDR1 as set forth in SEQ ID NO:7,
HCDR2 as set forth in SEQ ID NO:8,
HCDR3 as set forth in SEQ ID NO:9,
LCDR1 as set forth in SEQ ID NO:4,
LCDR2 as set forth in SEQ ID NO:5, and
LCDR3 as set forth in SEQ ID NO:6;
wherein HCDRs and LCDRs are defined according to Kabat.

In a third aspect, there is provided in the present application a bispecific antibody comprising an antigen-binding portion against human CD3E and an antigen-binding portion against human BCMA.

In some embodiments of the third aspect, the antigen-binding portion against human CD3E comprises:

HCDR1 as set forth in SEQ ID NO:1,
HCDR2 as set forth in SEQ ID NO:2,
HCDR3 as set forth in SEQ ID NO:3,
LCDR1 as set forth in SEQ ID NO:4,
LCDR2 as set forth in SEQ ID NO:5, and
LCDR3 as set forth in SEQ ID NO:6;
wherein HCDRs and LCDRs are defined according to Kabat.

In some embodiments of the third aspect, the antigen-binding portion against human BCMA comprises:

HCDR1 as set forth in SEQ ID NO:7,
HCDR2 as set forth in SEQ ID NO:8,
HCDR3 as set forth in SEQ ID NO:9,
LCDR1 as set forth in SEQ ID NO:4,
LCDR2 as set forth in SEQ ID NO:5, and
LCDR3 as set forth in SEQ ID NO:6;
wherein HCDRs and LCDRs are defined according to Kabat.

In some embodiments of the third aspect, the antigen-binding portion against human CD3E and the antigen-binding portion against human BCMA comprise the same light chain variable region.

In some specific embodiments of the third aspect, the antigen-binding portion against human CD3E and the antigen-binding portion against human BCMA comprise the same light chain. This embodiment facilitates proper assembly of the light and heavy chains and is also a preferred embodiment.

In some embodiments of the third aspect, the bispecific antibody is an IgG1 antibody comprising two heavy chain constant regions having the same hinge region, and the amino acid sequence of the hinge region is shown in SEQ ID NO:15, which replaces the sequences at positions 216-230 of the constant region of the natural human IgG1 antibody; the amino acid position of the antibody constant region is determined according to EU numbering.

In some embodiments of the third aspect, the bispecific antibody is an IgG1 antibody comprising a first heavy chain constant region and a second heavy chain constant region, wherein the amino acids at positions 354 and 366 of the first heavy chain constant region are C and W, respectively, and the amino acids at positions 349, 366, 368 and 407 of the second heavy chain constant region are C, S, A and V, respectively; the amino acid position of the antibody constant region is determined according to EU numbering.

When constructing a bispecific antibody that retains the Fc domain, the structure of the bispecific antibody can be optimized from the following two perspectives: heavy chain heteromerization and proper assembly of the light and heavy chains. In some embodiments, two Fc fragments comprise mutations that can ensure heavy chain heteromerization. The KIH (knob-in-hole) technique is a strategy to address heavy chain heteromerization. Generally, the KIH technique refers to the formation of a structure that facilitates pairing of the heterologous halves to each other by modifying the amino acid sequence of the CH3 region, which can maintain the structure of the normal antibody as much as possible while constituting the bispecific antibody. In some embodiments, the KIH technique utilized includes allowing the amino acids at positions 354 and 366 of one Fc fragment to be C and W, respectively, and the amino acids at positions 349, 366, 368 and 407 of the other Fc fragment to be C, S, A and V, respectively. For guidance on the KIH technique, see, for example, "An efficient route to human bispecific IgG", A. Margaret Merchant et al., Nature Biotechnology, Volume 16, 1998", which is incorporated herein by reference in its entirety.

In some embodiments of the third aspect, the bispecific antibody is an IgG1 antibody comprising a first heavy chain constant region and a second heavy chain constant region, wherein the amino acids at positions 234, 235 and 331 of the first and second heavy chain constant regions are F, E, and S, respectively; the amino acid position of the antibody constant region is determined according to EU numbering.

In some embodiments of the third aspect, the amino acids at positions 234, 235 and 331 of the CH2 fragment of the two heavy chain constant regions are F, E and S, respectively, which can reduce antibody dependent cytotoxicity (ADCC) mediated by the Fc segment of an antibody, thereby potentially reducing side effects caused by bispecific antibody in vivo. For guidance on the above mutations, see, for example, "The binding affinity of human IgG for its high affinity Fc receptor is determined by multiple amino acids in the CH2 domain and is modulated by the hinge region", Stephen M. Canfield et al., *J. Exp. Med*. Volume 173, 1991, which is incorporated herein by reference in its entirety.

In some embodiments of the first and third aspects, the antigen-binding portion against human CD3E comprises a heavy chain variable region as set forth in SEQ ID NO: 12 (comprising HCDR1 as set forth in SEQ ID NO:1, HCDR2 as set forth in SEQ ID NO:2, and HCDR3 as set forth in SEQ ID NO:3) and a light chain variable region as set forth in SEQ ID NO:14 (comprising LCDR1 as set forth in SEQ ID NO:4, LCDR2 as set forth in SEQ ID NO:5, and LCDR3 as set forth in SEQ ID NO:6).

In some embodiments of the second and third aspects, the antigen-binding portion against human BCMA comprises a heavy chain variable region as set forth in SEQ ID NO:10 (comprising HCDR1 as set forth in SEQ ID NO:7, HCDR2 as set forth in SEQ ID NO:8, and HCDR3 as set forth in SEQ ID NO:9) and a light chain variable region as set forth in SEQ ID NO: 14 (comprising LCDR1 as set forth in SEQ ID NO:4, LCDR2 as set forth in SEQ ID NO:5, and LCDR3 as set forth in SEQ ID NO:6).

In some embodiments of any of the above aspects, the antigen-binding portion against human CD3E comprises a single chain antibody (scfv) or a Fab fragment.

In some embodiments of any of the above aspects, the antigen-binding portion against human BCMA comprises a single chain antibody (scfv) or a Fab fragment.

As the bispecific antibody has two different antigen-binding portions against two different antigens, and the antigen-binding portions may comprise two forms of a single chain antibody (scfv) or a Fab fragment. The configuration of antigen-binding portions of the bispecific antibody may have four combinations for given two antigens: Fab+Fab, Fab+scfv, scfv+Fab, and scfv+scfv.

In some specific embodiments of any of the above aspects, the antigen-binding portion against human CD3E comprises a Fab fragment and the antigen-binding portion against human BCMA comprises a Fab fragment.

In some specific embodiments of any of the above aspects, the antigen-binding portion against human CD3E comprises a Fab fragment and the antigen-binding portion against human BCMA comprises a single chain antibody (scfv).

In some specific embodiments of any of the above aspects, the antigen-binding portion against human CD3E comprises a single chain antibody (scfv) and the antigen-binding portion against human BCMA comprises a Fab fragment.

In some specific embodiments of any of the above aspects, the antigen-binding portion against human CD3E comprises a single chain antibody (scfv) and the antigen-binding portion against human BCMA comprises a single chain antibody (scfv).

The bispecific antibody is also described herein as having two "arms". The bispecific antibody can be divided into two arms bounded by the central axis. The arms of the bispecific antibody can consist of an Fc fragment and an antigen-binding portion (Fab fragment or single chain antibody). For the arm consisting of an Fc fragment and an Fab fragment, its structure is similar to that of a common antibody, comprising intact heavy and light chains, and thus the structure of such an arm can be represented as Fc+Fab, or can be represented as a heavy chain (Fc+the heavy chain variable region of Fab and CH1 fragment)+a light chain (the light chain portion of Fab). When both arms contain the antigen-binding portions in the form of Fab fragment, the structure of the bispecific antibody thus formed is close to that of the native antibody and is a preferred embodiment.

In some embodiments of the third aspect, the antibody has a first arm and a second arm, wherein the first arm comprises an antigen-binding portion against human CD3E and the second arm comprises an antigen-binding portion against human BCMA:

- the first arm comprises the amino acid sequence of the heavy chain variable region as set forth in SEQ ID NO: 12, the amino acid sequence of the heavy chain constant region as set forth in SEQ ID NO: 19, the amino acid sequence of the light chain variable region as set forth in SEQ ID NO: 14, and the amino acid sequence of the light chain constant region as set forth in SEQ ID NO: 20;
- the second arm comprises the amino acid sequence of the heavy chain variable region as set forth in SEQ ID NO:10, the amino acid sequence of the heavy chain constant region as set forth in SEQ ID NO:18, the amino acid sequence of the light chain variable region as set forth in SEQ ID NO:14, and the amino acid sequence of the light chain constant region as set forth in SEQ ID NO:20.

In some embodiments of the third aspect, the antibody has a first arm and a second arm, wherein the first arm comprises an antigen-binding portion against human CD3E and the second arm comprises an antigen-binding portion against human BCMA:

- the first arm comprises the amino acid sequence of the heavy chain variable region as set forth in SEQ ID NO:12, the amino acid sequence of the heavy chain constant region as set forth in SEQ ID NO:37, the amino acid sequence of the light chain variable region as set forth in SEQ ID NO: 14, and the amino acid sequence of the light chain constant region as set forth in SEQ ID NO: 20;
- the second arm comprises the amino acid sequence of the heavy chain variable region as set forth in SEQ ID NO:10, the amino acid sequence of the heavy chain constant region as set forth in SEQ ID NO:38, the amino acid sequence of the light chain variable region as set forth in SEQ ID NO:14, and the amino acid sequence of the light chain constant region as set forth in SEQ ID NO:20.

In some embodiments of any of the above aspects, an exemplary antibody comprises a first arm comprising the amino acid sequences of SEQ ID NO: 39 and SEQ ID NO: 41 and a second arm comprising the amino acid sequences of SEQ ID NO: 40 and SEQ ID NO: 41. In some embodiments, the exemplary antibody is GR1803.

In some embodiments of any of the above aspects, the heavy chain constant region of the bispecific antibody is human IgG1 subtype or various mutants of a selected human IgG1 subtype, such as IgG1H, IgG1K, IgG1m3-H, or IgG1m3-K.

In some embodiments of any of the above aspects, the light chain constant region of the bispecific antibody is human 1c subtype or human X. subtype, preferably human 1c subtype.

In a fourth aspect, there is provided in the present application a pharmaceutical composition comprising the bispecific antibody of any one of the first to third aspects.

In some embodiments, the pharmaceutical composition further comprises a pharmaceutically acceptable carrier, excipient, diluent, and the like.

In some embodiments, the pharmaceutical composition is used to prevent or treat multiple myeloma.

In some embodiments, the pharmaceutical composition may further comprise a lubricant, such as talc, magnesium stearate, and mineral oil; a wetting agent; an emulsifier; a suspending agent; a preservative such as benzoic acid, sorbic acid and calcium propionate; a sweetening agent and/or a flavoring agent.

In some embodiments, the pharmaceutical composition of the present application may be formulated as a tablet, a pill, a powder, a lozenge, an elixir, a suspension, an emulsion, a solution, a syrup, a suppository, or a capsule.

In some embodiments, the pharmaceutical composition of the present application may be delivered using any physiologically acceptable administration route including, but not limited to, oral administration, parenteral administration, nasal administration, rectal administration, intraperitoneal administration, intravascular injection, subcutaneous administration, trans dermal administration, inhalation administration and the like.

In some embodiments, a pharmaceutical composition for therapeutic use may be formulated for storage in a lyophilized formulation or in the form of an aqueous solution by mixing an agent with desired purity with a pharmaceutically acceptable carrier or excipient where appropriate.

In a fifth aspect, there is provided in the present application use of the bispecific antibody of any one of the first to third aspects or the pharmaceutical composition of the fourth aspect in the manufacture of a medicament for the prevention or treatment of multiple myeloma.

In a sixth aspect, there is provided in the present application a method of preventing or treating multiple myeloma, comprising administering the bispecific antibody of any one of the first to third aspects or the pharmaceutical composition of the fourth aspect to a subject in need thereof.

It is to be understood that the foregoing detailed description is intended only to enable those skilled in the art to have better understanding of the present application and is not intended to cause limitations in any way. Various modifications and variations can be made to the described embodiments by those skilled in the art.

The following Examples are for purposes of illustration only and are not intended to limit the scope of the present application.

EXAMPLES

Example 1: Preparation of Recombinant Proteins

Many different recombinant proteins were required in the preparation and identification of CD3ExBCMA bispecific antibody, including the extracellular region of human CD3E (hCD3E, SEQ ID NO: 22), the extracellular region of human CD3D (hCD3D, SEQ ID NO: 23), the extracellular region of monkey CD3E (mfCD3E, SEQ ID NO: 24), the extracellular region of monkey CD3D (mfCD3D, SEQ ID NO: 25), the extracellular region of mouse CD3E (mCD3E, SEQ ID NO: 26), the extracellular region of mouse CD3D (mCD3D, SEQ ID NO: 27) and the extracellular region of human BCMA (hBCMA, SEQ ID NO: 28), the extracellular region of monkey BCMA (mfBCMA, SEQ ID NO: 29), and the extracellular region of mouse BCMA (mBCMA, SEQ ID NO: 30). These recombinant proteins all have a large number of post-translational modifications (e.g., glycosylation or disulfide bonds, etc.), and thus the use of the mammal cell expression system would be more advantageous in maintaining the structures and functions of the recombinant proteins. Furthermore, for ease of purification, His tags (SEQ ID NO: 31) or Fc fragments of mouse antibody IgG2a (mFc, SEQ ID NO: 32) were added to the C-terminus of the non-antibody recombinant proteins, or Fc mutants (FcK, SEQ ID NO: 33 or FcH, SEQ ID NO: 34) of human IgG1 subtype of heterodimer were formed based on KIH (Knob-Into-Hole) technique. In the preparation of recombinant antibody, the heavy chain constant region of the antibody can be human IgG1 subtype (SEQ ID NO: 35) or various mutants of the selected human IgG1 subtype, such as IgG1H (SEQ ID NO: 36), IgG1K (SEQ ID NO: 17), IgG1m3-H (SEQ ID NO: 18) or IgG1m3-K (SEQ ID NO: 19), and the light chain constant region can be human 1c subtype (SEQ ID NO: 20) or human X subtype (SEQ ID NO: 21).

Based on the amino acid sequences of various recombinant proteins of interest recorded in the Uniprot database, the genes (comprising His-tag, mFc or Fc encoding gene) of the above recombinant proteins were designed and synthesized. By conventional molecular biology techniques, the synthesized genes encoding the recombinant proteins were cloned into proper eukaryotic expression vectors (e.g., pcDNA3.1 from Invitrogen Inc.). Then, liposomes (e.g., 293fectin from Invitrogen Inc.) or other transfection agents (e.g., PEI) were used to transfect the recombinant protein expression plasmids as prepared into HEK293 cells (e.g., HEK293F from Invitrogen Inc.). The cells were incubated in suspension under serum-free condition for 3-5 days. Then, the supernatant of the culture was harvested by centrifugation.

For recombinant proteins fused with His-tags, the recombinant proteins in the supernatant were further purified using metal chelate affinity chromatography columns (e.g., HisTrap FF from GE Inc.). The recombinant proteins and antibodies fused with mFc were further purified using a Protein A/G affinity chromatography column (e.g., Mab select SURE from GE Inc.). Then, the recombinant protein preservation buffer was then replaced with PBS buffer (pH 7.0) or other suitable buffers using a desalination column (e.g., Hitrap desaulting, GE Inc.). If necessary, the antibody samples can be sterilized by filtration and then stored in aliquots at −20° C. for later use.

Example 2: Screening and Identification of Common Light Chains 2.1 Screening of Common Light Chains H10B7+L1G10 is a monoclonal antibody that binds to human CD3E obtained by using human antibody library technique. The amino acid sequence of the heavy chain variable region H10B7 of H10B7+L1G10 is shown in SEQ ID NO: 12 and the amino acid sequence of the light chain variable region L1G10 is shown in SEQ ID NO: 13 (see the amino acid sequences as set forth in SEQ ID NO: 19 and SEQ ID NO: 20 in Chinese Patent Application No. 201910372193.6).

C4 is a monoclonal antibody targeting the tumor antigen BCMA, the amino acid sequence of the heavy chain variable region C4VH is shown in SEQ ID NO: 11, and the amino acid sequence of the light chain variable region C4VK is shown in SEQ ID NO: 16 (see the sequence of the monoclonal antibody CA8-J7M0 in U.S. Pat. No. 9,273,141B2).

The functions and properties of the monoclonal antibodies C4 and H10B7+L1G10 have been experimentally confirmed.

Based on the established dual-vector system for the phage display, the original light chain library was subjected to two rounds of screening and enrichment on the basis of the heavy chain variable region H10B7 of the anti-CD3E monoclonal antibody H10B7+L1G10 with CD3E/CD3D as a screening antigen by using the light chain replacement strategy (see Example 4 in Chinese Patent Application No. 201510097117.0 for detailed experimental protocols). Next, the light chain library enriched by CD3E/CD3D was subjected to two rounds of screening and enrichment on the basis of the heavy chain of the anti-BCMA monoclonal antibody C4 with BCMA as the antigen. Finally, the resultant light chain was identified to obtain the common light chain variable region L9B9 (SEQ ID NO: 14), which can simultaneously maintain the activity of both the anti-CD3E antibody and the anti-BCMA antibody.

The heavy chain variable region H10B7, the heavy chain variable region C4VH of C4, and the light chain variable region L9B9 were respectively cloned into eukaryotic expression vectors fused with human IgG1 heavy chain constant region and the x light chain constant region by using conventional molecular biological means, so as to express complete antibodies H10B7+L9B9 and C4VH+L9B9 in combination.

2.2 Determination of the Binding Affinity of the Anti-BCMA Antibody C4VH+L9B9 with Common Light Chain to Human BCMA.

The affinity of anti-BCMA antibodies (C4 and C4VH+L9B9) was determined by surface plasmon resonance technique using Biacore X100. Reagents and consumables such as amino coupling kit (BR-1000-50), human antibody capture kit (BR-1008-39), CM5 chip (BR100012), and 10×HBS-EP, pH 7.4 (BR100669) were purchased from GE healthcare. The surface of the carboxylated CM5 chip was activated with 1-ethyl-3-(3-dimethylaminopropyl) carbodiimide hydrochloride (EDC) and N-hydroxysuccinimide (NHS) according to the instructions in the kit. The anti-human IgG (Fc) antibody (capture antibody) was diluted to 25 μg/mL with 10 mM sodium acetate solution (pH 5.0), followed by injection at a flow rate of 10 μL/min to achieve a coupling amount of approximately up to 10,000 response units (RU). After injection of the capture antibody, 1 M ethanolamine was injected to block unreacted groups. For kinetic measurement, the anti-BCMA antibody was diluted to 0.5-1 μg/mL, followed by injection at a flow rate of 10 μL/min to ensure that about 400 RU of the antibody was captured by the anti-human Fc antibody. Next, a series of concentration gradients for hBCMA-his were set (for example, 0.617 nM, 1.85 nM, 5.56 nM, 16.7 nM, and 50 nM), and were injected from low concentration to high concentration at 30 μL/min at 25° C. The association time was 120 s, and the dissociation time was 1800 s. The surface of the chip was regenerated by injection of 3 M $MgCl_2$ solution at 10 μL/min for 30 s. The association rate (Kon) and dissociation rate (Koff) were calculated by fitting the association and dissociation sensorgrams with a 1:1 association model using the Biacore X100 evaluation software, version 2.0.1. The dissociation equilibrium constant (KD) was calculated as the ratio Koff/Kon. The fitting results are shown in Table 1.

TABLE 1

Affinity constants of binding of anti-BCMA antibodies to human BCMA

| | Kon | Koff | KD |
|---|---|---|---|
| C4 | 4.333E+5 | 7.948E−5 | 1.834E−10 |
| C4VH + L9B9 | 3.238E+5 | 9.554E−4 | 2.950E−9 |

Example 3: The Affinity Maturation of Anti-BCMA Antibody 3.1 Screening of the Heavy Chain Mutation Library of C4

A CDR3 mutant library based on the heavy chain variable region C4VH was constructed by introducing a mutation in the CDR3 region of the heavy chain variable region C4VH using conventional molecular biological means. The designed mutation scheme is shown in Table 2, and the 1.2×10E8 of library capacity was created with an accuracy of 86.7%.

TABLE 2

Mutation scheme of CDR3 mutant library based on the heavy chain variable region C4VH of C4
C4VH-CDR3: 1.8 × 10E7 diversity

| Initial amino acid | Mutant amino acid | Degenerate code |
|---|---|---|
| G | Q A or D | GVT |
| A | A, T, N, D, S or G | RVC |
| I | L, F, IorV | NTC |
| Y | F, S, Y, I, T or N | WHC |
| D | D, Y, S or A | KMC |
| G | Q A or D | GVT |
| Y | For Y | TWC |
| D | D, E, AorG | GVM |
| V | L, F, IorV | NTC |
| L | L, F, I or V | NTC |
| D | D, N, S, T, A or G | RVC |
| N | N, D, Y, S, AorT | DMC |

Based on the dual-vector system for the phage display (see Example 5 in Chinese Patent Application No. 201510097117.0), the constructed C4VH-CDR3 mutant library was subjected to three rounds of screening and enrichment with the hBCMA-His antigen by solid phase screening method. Finally, the heavy chain variable region mutant H13F1 (SEQ ID NO:10) with increased affinity was obtained.

3.2 Affinity Assay of the Heavy Chain Mutant of C4

The nucleotide sequences encoding the heavy chain variable region mutant H13F1 of C4 and the light chain variable region L9B9 were respectively cloned into eukaryotic expression vectors fused with the nucleotide sequences encoding the human heavy chain constant region and the light chain constant region by using conventional molecular biological means, so as to express complete antibodies in combination. Referring to Example 2.2, the mutant of C4 (IgG1 subtype) was subjected to affinity assay by using Biacore X100, and the result is shown in Table 3.

TABLE 3

| Affinity constants of binding of anti-BCMA antibodies to human BCMA | | | |
|---|---|---|---|
| | Kon | Koff | KD |
| C4VH + L9B9 | 5.307E+5 | 8.156E−4 | 1.537E−9 |
| H13F1 + L9B9 | 7.85E+5 | 4.284E−4 | 5.429E−10 |

Example 4: Preparation of Bispecific Antibodies

The nucleotide sequences encoding the heavy chain variable region H10B7 of the anti-CD3E monoclonal antibody and the heavy chain variable region H13F1 of the anti-BCMA monoclonal antibody were respectively cloned into suitable eukaryotic expression vectors to construct heterodimers based on the common light chain. That is, the nucleotide sequence encoding the heavy chain variable region of the anti-CD3E antibody was cloned into eukaryotic expression vectors fused with the nucleotide sequence encoding the IgG1 constant region with Knob mutation IgG1m3-K, the nucleotide sequence encoding the heavy chain variable region of the anti-BCMA antibody was cloned into eukaryotic expression vectors containing the nucleotide sequence encoding the IgG1 constant region with Hole mutation IgG1m3-H, and the nucleotide sequence encoding the variable region VK of the common light chain L9B9 was cloned into eukaryotic expression vectors fused with the nucleotide sequence encoding the human light chain constant region CK.

The three constructed eukaryotic expression vectors expressing H10B7-IgGlm3-K, H13F1-IgG1m3-Hand L9B9VK-CK were co-transfected into HEK293F cells using liposomes, and the cells were cultured in suspension in a serum-free medium for 3-5 days. The supernatant of the culture was harvested by centrifugation. The bispecific antibodies in the culture supernatant were purified using a Protein A/G affinity chromatography column (e.g., Mabselect SURE, GE Inc.). The recombinant protein preservation buffer was then replaced with PBS buffer (pH 7.0) or other suitable buffers using a desalination column (e.g., Hitrap desaulting, GE Inc.). The desalted protein solution was purified by a size exclusion chromatography (SEC) using Superdex 200 (GE), thereby obtaining the protein of interest. If necessary, the antibody samples can be sterilized by filtration and then stored in aliquots at −20° C. for later use.

Example 5: Affinity Assay of Bispecific Antibodies

Referring to Example 2.2, the affinity assays were performed on anti-BCMA monoclonal antibody H13F1+L9B9, anti-CD3E monoclonal antibody H10B7+L9B9, and bispecific antibody CD3ExBCMA by surface plasmon resonance technique using Biacore X100.

When the affinity of the anti-BCMA monoclonal antibody and the CD3ExBCMA bispecific antibody to the BCMA antigen was determined, the anti-human IgG (Fc) antibody was conjugated to the surface of the CM5 chip. The antibody protein was diluted to 0.5-1 μg/ml, and was injected at 10 μL/min. About 400 RU of the BCMA monoclonal antibody was ensured to be captured by the anti-human Fc antibody, and about 800 RU of the bispecific antibody CD3ExBCMA was ensured to be captured by the anti-human Fc antibody. Next, a series of concentration gradients for BCMA-his were set (for example, 0.617 nM, 1.85 nM, 5.56 nM, 16.7 nM, and 50 nM), and were injected from low concentration to high concentration at 30 μL/min at 25° C. The association time was 120 s, and the dissociation time was 1800 s. The surface of the chip was regenerated by injection of 3 M $MgCl_2$ solution at 10 μL/min for 30 s. The results of affinity fit are shown in Table 4 and Table 5.

TABLE 4

| Affinity constants of binding of anti-BCMA monoclonal antibody H13F1 + L9B9 and the bispecific antibody CD3 × BCMA to human BCMA | | | |
|---|---|---|---|
| | Kon | Koff | KD |
| H13F1 + L9B9 | 1.174E+6 | 4.161E−4 | 3.544E−10 |
| CD3E × BCMA | 1.063E+6 | 3.236E−4 | 3.045E−10 |

TABLE 5

| Affinity constants of binding of anti-BCMA monoclonal antibody H13F1 + L9B9 and the bispecific antibody CD3 × BCMA to monkey BCMA | | | |
|---|---|---|---|
| | Kon | Koff | KD |
| H13F1 + L9B9 | 6.63E+5 | 3.289E−3 | 4.961E−9 |
| CD3E × BCMA | 6.551E+5 | 3.26E−3 | 4.976E−9 |

When the affinity of the anti-CD3E monoclonal antibody and the bispecific antibody CD3ExBCMA to the CD3E antigen was determined, the anti-human Fab antibody (Human Fab Capture Kit, GE, 28-9583-25) was conjugated to the surface of the CM5 chip. The antibody protein was diluted to 0.5-1 μg/ml, and was injected at 10 μL/min. About 70 RU of the anti-CD3E monoclonal antibody was ensured to be captured by the anti-human Fab antibody, and about 150 RU of the bispecific antibody CD3ExBCMA was ensured to be captured by the anti-human Fab antibody. A series of concentration gradients for human CD3E heterodimer CD3E-FcK/CD3D-FcH were set (for example, 12.5 nM, 25 nM, 50 nM, 100 nM, and 200 nM), and were injected from low concentration to high concentration at 30 μL/min at 25° C. The association time was 120 s, and the dissociation time was 600 s. The surface of the chip was regenerated by injection of 10 mM glycine-HCl (pH 2.1) at 10 μL/min for 60 s. The results of affinity fit are shown in Table 6.

TABLE 6

| Affinity constants of binding of anti-CD3E monoclonal antibody H10B7 + L9B9 and the bispecific antibody CD3E × BCMA to human CD3E | | | |
|---|---|---|---|
| | Kon | Koff | KD |
| H10B7 + L9B9 | 1.750E+5 | 3.075E−3 | 1.757E−8 |
| CD3E × BCMA | 1.179E+5 | 2.838E−3 | 2.408E−8 |

Example 6: Identification of the Ability of Bispecific Antibodies to Simultaneously Recognize Both CD3E and BCMA Antigens The ability of the bispecific antibody CD3ExBCMA (CD3ExBCMA BsAb) to simultaneously bind to both CD3E and BCMA antigens was detected using conventional ELISA methods.

A 96-well ELISA plate was coated with CD3E-FcK/CD3D-FcH antigen (3 μg/mL, 100 μL/well), and was coated overnight in a refrigerator at 4° C. After being blocked with blocking solution PBS-0.1% Tween 20-3% milk at 37° C. for 1 hour, the anti-BCMA monoclonal antibody H13F1+L9B9, the anti-CD3E monoclonal antibody H10B7+L9B9 and the bispecific antibody CD3ExBCMA (10 μg/mL, 100 μL/well) were respectively added to the plate in duplicate, and incubated at 37° C. for 1 hour. The ELISA plate was washed with PBS-0.1% Tween 20, followed by addition of BCMA-His antigen (1 μg/mL, 100 μL/well) and incubation at 37° C. for 1 hour. The ELISA plate was washed with PBS-0.1% Tween 20, followed by addition of HRP mouse anti-his IgG (Beijing ComWin Biotech Co., Ltd., cw0285M) and incubation at 37° C. for 1 hour. The ELISA plate was washed with PBS-0.1% Tween 20, and OPD substrate color development solution was added. The color development was terminated with 1 M H2SO4 after 5-10 minutes. The optical density value at 492 nm/630 nm dual wavelength was measured using a microplate reader. The result of ELISA assay is shown in FIG. 1. The bispecific antibody CD3ExBCMA can simultaneously recognize both CD3E and BCMA antigens.

Figure 2:
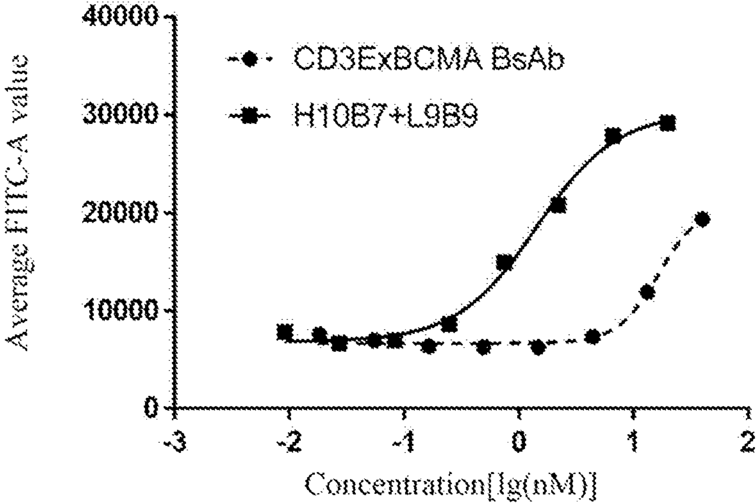
FIG. 2 shows the results of analyzing the binding of the bispecific antibody CD3ExBCMA to CD3E on the surface of Jurkat human acute T lymphocyte leukemia cell by using flow cytometry.

Example 7: Identification of the Ability of Bispecific Antibodies to Recognize CD3E and BCMA on Cell Surfaces Jurkat human acute T-lymphocyte leukemia cells (Cell Resource Center, Institute of Basic Medicine, Chinese Academy of Medical Sciences) in the logarithmic growth phase were harvested, centrifuged, and resuspended in PBS buffer containing 1% BSA to $2\times10^6$ cells/mL, and plated at 100 μL/well in 96-well V bottom plates. The anti-CD3E monoclonal antibody H10B7+L9B9 and the bispecific antibody CD3ExBCMA were taken for gradient dilution. The anti-CD3E monoclonal antibody had an initial concentration of 3 μg/mL, and was diluted by 3-fold gradient, with a total of 8 concentration points. The bispecific antibody had an initial concentration of 6 μg/mL, was diluted by 3-fold gradient, with a total of 8 concentration points. 100 μL of the anti-CD3E monoclonal antibody or 100 μL of the bispecific antibody was added to the wells containing cells and incubated at 4° C. for 1 hour. Next, the cells were washed three times with 200 μL of PBS solution and incubated with goat anti-human IgG-FITC (Beijing Zhongshan Golden Bridge Biotechnology Co., Ltd., ZF-0308) (100 μL/well) at 4° C. for 30 minutes in the dark. Next, the cells were washed three times with 200 μL of PBS solution, and suspended in 100 μL of PBS solution. Thereafter, the FITC channel was detected by flow cytometer (ACEA, Novocyte). The results showed that the bispecific antibody CD3ExBCMA can bind well to CD3 positive Jurkat cells (FIG. 2). The KD value of the bispecific antibody CD3ExBCMA was 16.79 nM, and the KD value of the anti-CD3E monoclonal antibody was 1.43 nM.

Figure 3:
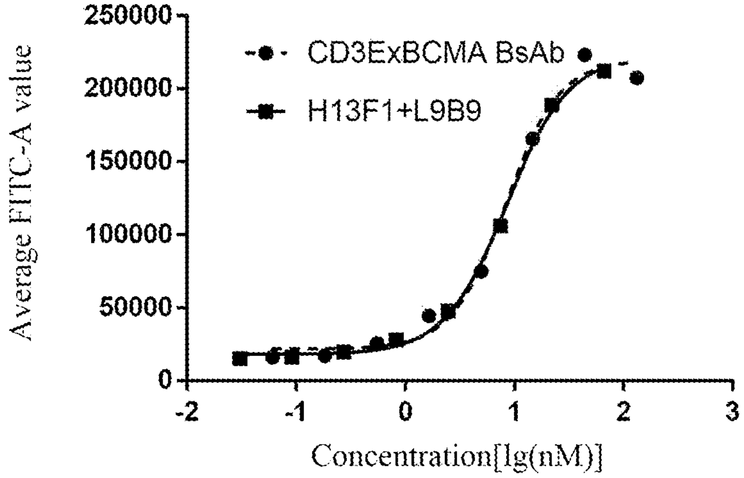
FIG. 3 shows the results of analyzing the binding of the bispecific antibody CD3ExBCMA to BCMA on the surface of NCI-H929 human plasma cell leukemia cell by using flow cytometry.

NCI-H929 human plasma cell leukemia cells (Cell Resource Center, Institute of Basic Medicine, Chinese Academy of Medical Sciences) in logarithmic growth phase were harvested, centrifuged, and resuspended in PBS buffer containing 1% BSA to $2\times10^6$ cells/mL, and plated at 100 μL/well in 96-well V bottom plates. The anti-BCMA monoclonal antibody H13F1+L9B9 and the bispecific antibody CD3ExBCMA were taken for gradient dilution. The anti-BCMA monoclonal antibody had an initial concentration of 10 μg/mL, was diluted by 3-fold gradient, with a total of 8 concentration points. The bispecific antibody had of an initial concentration of 20 μg/mL, was diluted by 3-fold gradient, with a total of 8 concentration points. 100 μL of the anti-BCMA monoclonal antibody or 100 μL of the bispecific antibody was added to the wells containing cells and incubated at 4° C. for 1 hour. Next, the cells were washed three times with 200 μL of PBS solution and incubated with goat anti-human IgG-FITC (Beijing Zhongshan Golden Bridge Biotechnology Co., Ltd., ZF-0308) (100 μL/well) at 4° C. for 30 minutes in the dark. Next, the cells were washed three times with 200 μL of PBS solution, and suspended in 100 μL of PBS solution. Thereafter, the FITC channel was detected by flow cytometer (ACEA, Novocyte). The results showed that the bispecific antibody CD3ExBCMA can bind well to BCMA positive NCI-H929 cells (FIG. 3). The KD value of the bispecific antibody CD3ExBCMA was 8.27 nM, and the KD value of the anti-BCMA monoclonal antibody was 8.47 nM.

Figure 4:
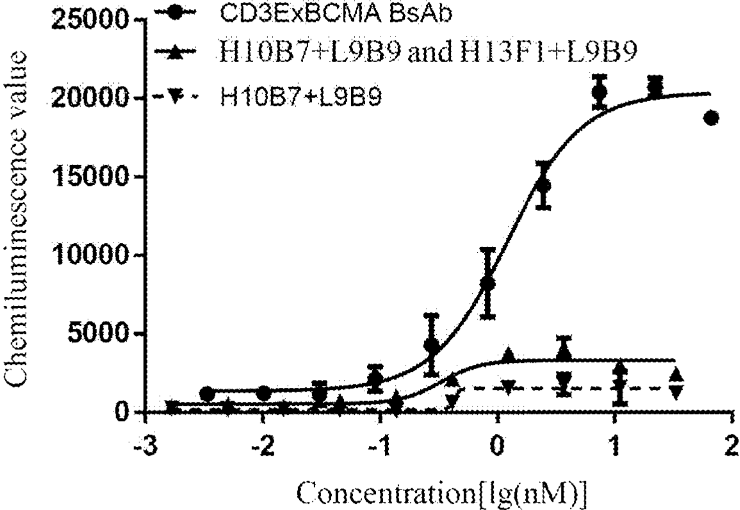
FIG. 4 shows the specific activation of jurkat-dual cells by BCMA-positive tumor cells mediated by the bispecific antibody CD3ExBCMA.

Example 8: Bispecific Antibody Mediates Specific Activation of Jurkat-Dual Cells by BCMA Positive Tumor Cells NCI-H929 human plasma cell leukemia cells (high expression of BCMA, purchased from Cell Resource Center, Institute of Basic Medicine, Chinese Academy of Medical Sciences) in logarithmic growth phase were collected. After centrifugation, the cells were resuspended with 1640 medium to $4\times10^5$ cells/mL and plated in the cell plate at 50 μL/well. Jurkat-dual cells (purchased from Invivogen) in logarithmic growth phase were collected, centrifugated, and resuspended with 1640 medium to $1\times10^6$ cells/mL, and were added to the cell plate with 100 μL/well to obtain a final ET ratio of 5:1. The bispecific antibody CD3ExBCMA (50 μL/well), the anti-CD3E monoclonal antibody H10B7+L9B9 (50 μL/well) or a combination of the anti-CD3E monoclonal antibody H10B7+L9B9 and the anti-BCMA monoclonal antibody H13F1+L9B9 was then added to the cell plate, wherein the bispecific antibody had an initial concentration of 10 μg/mL, and was diluted by 3-fold gradient, with a total of 10 concentration point; the anti-CD3E monoclonal antibody H10B7+L9B9 had an initial concentration of 5 μg/mL, and was diluted by 3-fold gradient, with a total of 10 concentration points; and for the combination of the anti-CD3E monoclonal antibody H10B7+L9B9 and the anti-BCMA monoclonal antibody H13F1+L9B9, each of which had an initial concentration of 5 μg/mL, and was diluted by 3-fold gradient, with a total of 10 concentration points. After 20 hours of incubation, the supernatant was taken and the specific activation of Jurkat-Dual cells by BCMA-positive tumor cells mediated by the bispecific antibody CD3ExBCMA, the anti-CD3E monoclonal antibody, and the combination of the anti-CD3E monoclonal antibody and the anti-BCMA monoclonal antibody were detected and analyzed with reference to the instructions of QUANTI-Luc™ (QUANTI-Luc™, Invivogen, rep-q1c2). The results show that only the bispecific antibody CD3ExBCMA can mediate activation of Jurkat-Dual cells by BCMA-positive tumor cells, and neither anti-CD3E monoclonal antibody alone nor the combination of anti-CD3E monoclonal antibody and anti-BCMA monoclonal antibody can mediate activation of Jurkat-Dual cells by BCMA-positive tumor cells (FIG. 4).

Example 9: Bispecific Antibody Mediates the Killing of BCMA Positive Tumor Cells by T Cells 9.1 Isolation of Human Peripheral Blood Mononuclear Cells (PBMCs)

Blood (50 mL each) was collected from normal volunteers. The collected blood was provided by the inventors and their colleagues as volunteers, all of whom had signed informed consent. Inclusion criteria for volunteers were as follow:

Age older than 18 years;
No HIV and HBV infection;
Normal blood routine test;
Non-pregnant or non-lactating women.

PBMCs were isolated from whole blood of the volunteers using Ficoll density gradient centrifugation and were cultured in 1640 medium.

9.2 Detection of PBMCs Killing BCMA Positive Tumor Cells Mediated by Bispecific Antibody NCI-H929 human plasma cell leukemia cells (high expression of BCMA), RPMI-8226 human multiple myeloma cells (moderate expression of BCMA), and HL60 human acute promyelocytic leukemia cells (BCMA negative) were purchased from the Cell Resource Center, Institute of Basic Medicine, Chinese Academy of Medical Sciences. The cells in the logarithmic growth phase were collected, centrifuged, and resuspended in 1640 medium to $4\times10^5$ cells/mL, and were plated in cell plates at 50 μL/well. Next, the bispecific antibody CD3ExBCMA, which had an initial concentration of 1 μg/mL and was diluted by 4-fold gradient with a total of 10 concentration points, was added (50 μL/well) to the cell plate. Finally, 100 μL/well of PBMCs (effectors) were added to obtain a final ET ratio of 5:1. Meanwhile, target cell control alone (NCI-H929 cells, RPMI-8226 cells, or HL60 cells), effector cell control alone (PBMCs), and medium blank control alone were set and the volumes thereof were replenished to 200 μL with medium. After 20 hours of incubation, the supernatant was taken. The killing rate of T cells to tumor cells mediated by the bispecific antibody was detected and analyzed with reference to the instructions of the cytoTox96® Non-Radioactive Cytotoxicity Assay (Promega, G1780).

Figure 5:
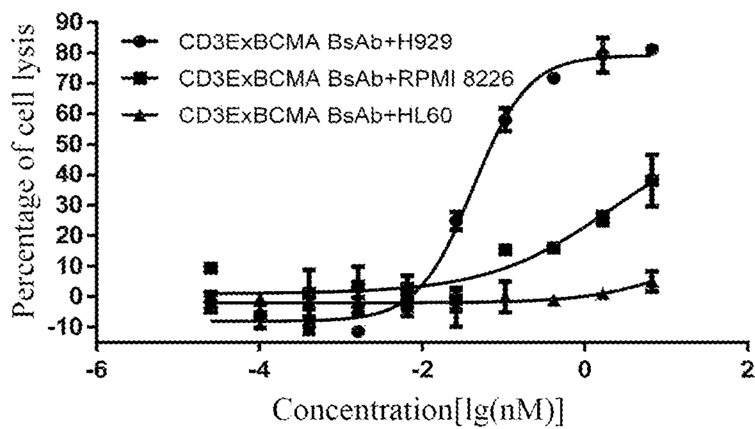
FIG. 5 shows the killing effect of PBMC on BCMA-positive tumor cells mediated by the bispecific antibody CD3ExBCMA.

The results showed that in the presence of the bispecific antibody CD3ExBCMA, the effector cells had a significant killing effect on the highly expressed NCI-H929 cells and the moderately expressed RPMI-8226 cells, but had no killing effect on the negative HL60 (FIG. 5), indicating that the bispecific antibody CD3ExBCMA can effectively mediate the killing of T cells to cells with different positive expression levels of BCMA, and cannot mediate the killing of BCMA negative cells.

Example 10: Bispecific Antibodies can Specifically Stimulate the Expression of Activation Molecule on the Surface of T Cells NCI-H929 human plasma cell leukemia cells (high expression of BCMA), RPMI-8226 human multiple myeloma cells (moderate expression of BCMA), and HL60 human acute promyelocytic leukemia cells (BCMA negative) in logarithmic growth phase were collected, centrifuged, and resuspended in 1640 medium to $4\times10^5$ cells/mL, and were plated in cell plates at 50 μL/well. Next, the bispecific antibody CD3ExBCMA, which had an initial concentration of 1 μg/mL and was diluted by 4-fold gradient with a total of 10 concentration points, was added (50 μL/well) to the cell plate. Finally, 100 μL/well of PBMCs (effectors) were added to obtain a final E:T ratio of 5:1. After 20 hours of incubation, the cells were centrifuged at 350 g for 5 minutes, washed once with PBS, and incubated with flow cytometry antibodies, i.e., anti-human CD3 (Ebioscience, 17-0037-42) and anti-human CD69 (Ebioscience, 11-0069-42) at 4° C. for 30 minutes in the dark. Then the cells were washed twice with 200 μL PBS solution, resuspended in 100 μL PBS solution and detected by flow cytometer (ACEA, Novocyte) to compare the difference in the expression of the activation marker CD69 of the CD3 positive cell population after treatment with the bispecific antibody CD3ExBCMA.

Figure 6:
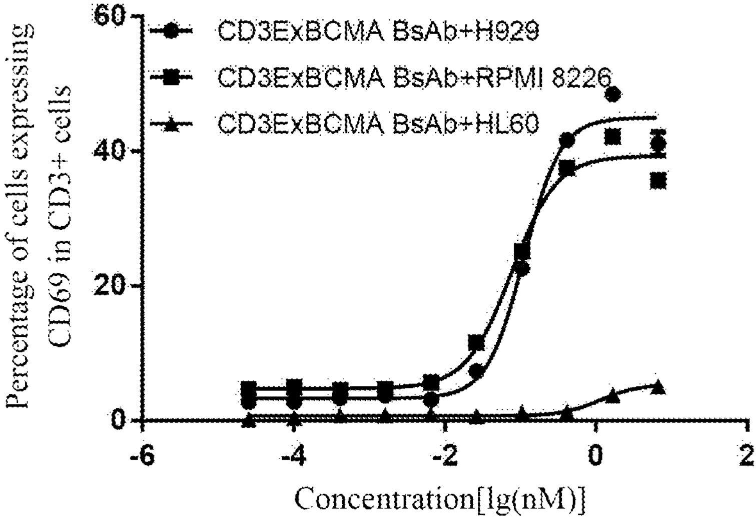
FIG. 6 shows the results of the bispecific antibody CD3ExBCMA stimulating CD69 expression on the surface of T cells in the presence of BCMA-positive tumor cells.

The results showed that the bispecific antibody CD3ExBCMA can specific activate T cells in the presence of NCI-H929 with high expression of BCMA or RPMI-8226 with moderate expression of BCMA, and the bispecific antibody CD3ExBCMA cannot activate T cells in the presence of FIL60 with negative BCMA (FIG. 6), indicating that the bispecific antibody CD3ExBCMA can effectively activate T cells in the presence of cells with different positive expression levels of BCMA, and cannot activate T cells in the presence of BCMA negative cells.

Example 11: Antitumor Activity of Bispecific Antibody in PBMC Immune Reconstitution Mouse Model Blood (50 mL each) was collected from normal volunteers. The collected blood was provided by the inventors and their colleagues as volunteers, all of whom had signed informed consent. Inclusion criteria for volunteers were as follow:

Age older than 18 years;
No HIV and HBV infection;
Normal blood routine test;
Non-pregnant or non-lactating women.

Human peripheral blood mononuclear cells (PBMCs) were isolated from healthy human peripheral blood using Ficoll density gradient centrifugation. Twenty-five female NPG mice aged 78 weeks (Beijing Viktor Biotechnology Co., Ltd.) were selected. $5><10^6$ NCI-H929 cells were subcutaneously inoculated on the right side of NPG mice, and the day of inoculation was defined as day 0. Two hours after tumor cell inoculation, each mouse was inoculated intraperitoneally with $5\times10^6$ of individual PBMCs. When the average tumor volume reached to 95 $mm^3$, the mice were randomly divided into three groups according to the tumor sizes. The test groups can be divided into 3 groups: group 2, the bispecific antibody CD3ExBCMA, 0.1 mg/kg; group 3, the bispecific antibody CD3ExBCMA, 0.02 mg/kg; and group 1, the solvent control group. Each group consists of six mice. The bispecific antibody was administered once via tail vein injection. Four days after the first administration, the dose of group 2 was changed to 0.5 mg/kg, the dose of group 3 was changed to 0.1 mg/kg, and the bispecific antibody was administered three more times at the frequency of twice a week. The therapeutic effects were evaluated according to the relative tumor growth inhibition value (TGI), and the safety was evaluated according to the body weight change and death of animals.

Figure 7:
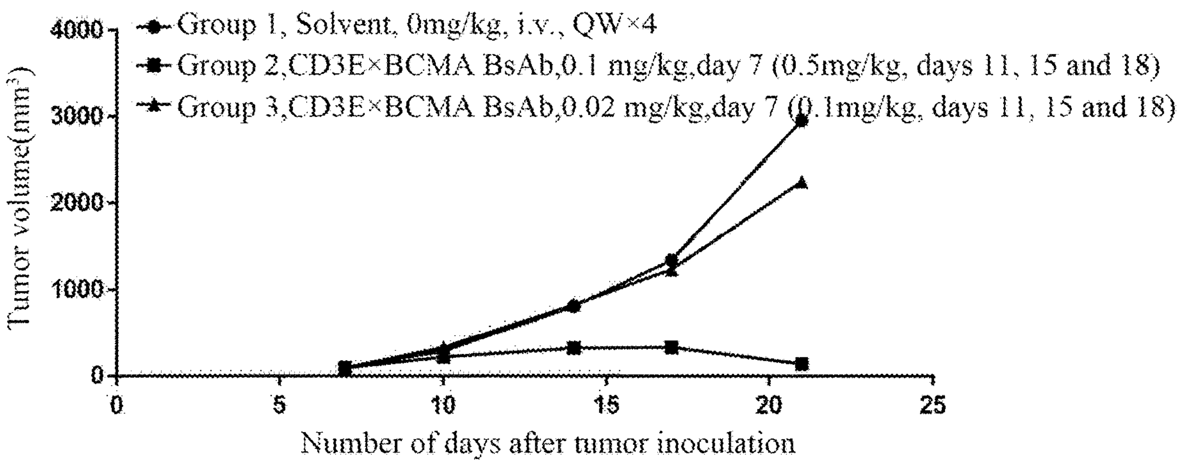
FIG. 7 shows the changes in tumor volume of a PBMC humanized mouse model with NCI-H929 human-derived myeloma treated with the bispecific antibody CD3ExBCMA.
Figure 8:
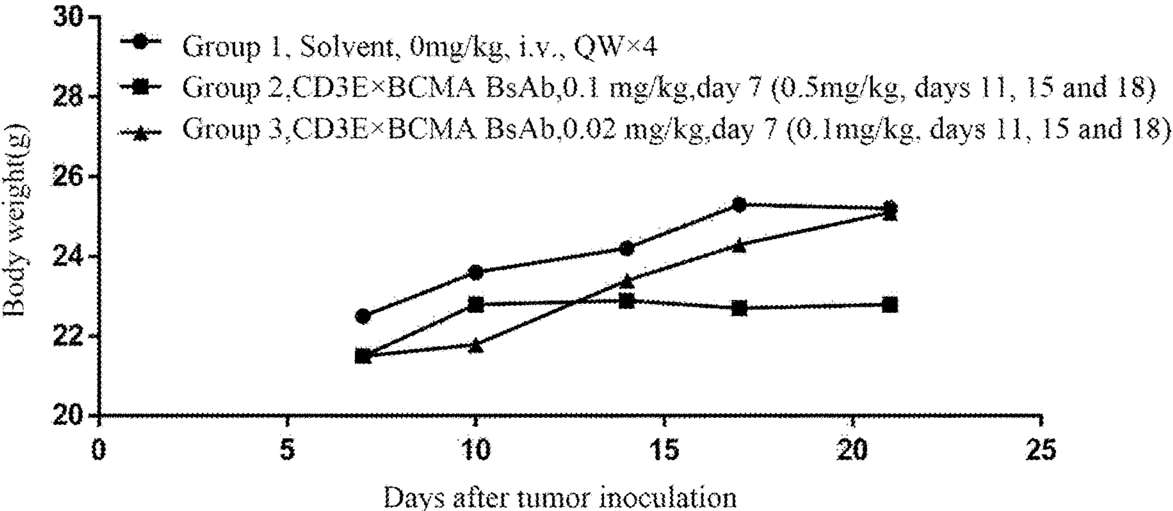
FIG. 8 shows the changes in body weight of a PBMC humanized mouse model with NCI-H929 human-derived myeloma treated with the bispecific antibody CD3ExBCMA.

The results showed that the bispecific antibody CD3ExBCMA significantly inhibited tumor growth at a dose of 0.1/0.5 mg/kg with TGI (%) of 95%, $p<0.001$ (FIG. 7). Meanwhile, at the doses of 0.02/0.1 mg/kg and 0.1/0.5 mg/kg of the bispecific antibody CD3ExBCMA, there were no animal deaths and no obvious drug toxicity in each treatment group, and the animals were well tolerated during treatment (FIG. 8).

Example 12: Antitumor Activity of Bispecific Antibody in hCD34+ Humanized Mice Model Twenty female hCD34+ humanized mice aged 20-24 weeks (purchased from Pengli Biomedical Technology (Shanghai) Co., Ltd) were selected. 100 μL of $1\times10^7$ RPMI8226 cells and 100 μL of Matrigel were mixed well, and then the mixture was inoculated into the right side of the back of the mice via subcutaneous injection. The mice were anesthetized with 3-4% isoflurane before inoculation. When the average tumor volume reached to about 50-80 $mm^3$, 16 tumor-bearing mice were randomly divided into 2 groups according to the ratio of hCD34+ in the peripheral blood and the tumor volumes, with 8 mice in each group. The day of grouping and administration was defined as day 0. The test groups can be divided into 2 groups: administration group, the bispecific antibody CD3ExBCMA, 0.01 mg/kg and negative control group, IgG1m3, 0.01 mg/kg. Each group consists of eight mice. The bispecific antibody was administered via tail vein injection, with a total of 4 times at the frequency of once a week. The therapeutic effects were evaluated according to the relative tumor growth inhibition value (TGI), and the safety was evaluated according to the body weight change and death of animals.

Figure 9:
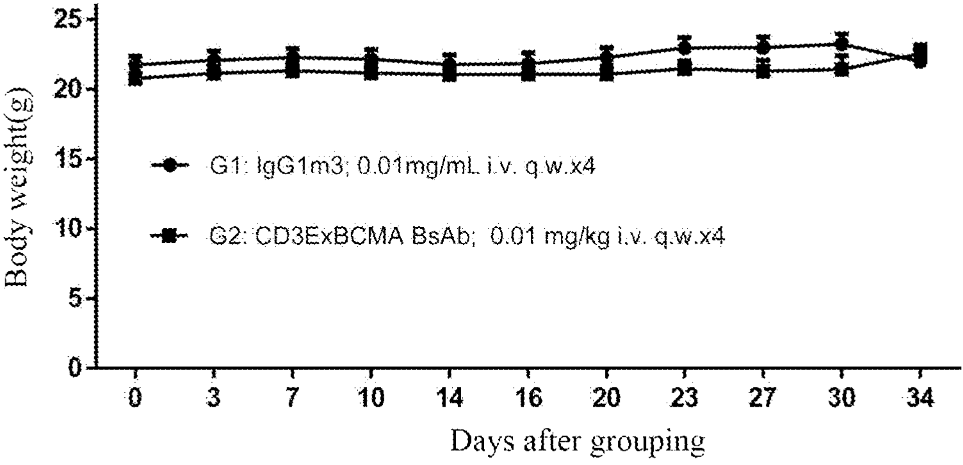
FIG. 9 shows the changes in body weight of a hCD34+ humanized mouse model with RPMI-8226 human-derived myeloma treated with the bispecific antibody CD3ExBCMA.
Figure 10:
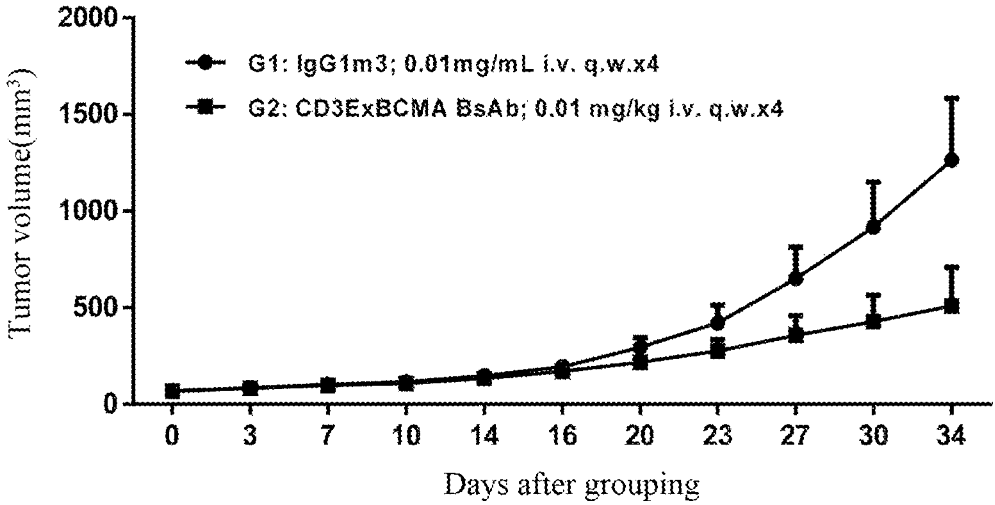
FIG. 10 shows the changes in tumor volume of a hCD34+ humanized mouse model with RPMI-8226 human-derived myeloma treated with the bispecific antibody CD3ExBCMA.

During the experiment, the animals were generally in good mental states. At the end of the in vivo experiment (day 34), there was no significant difference in body weight (P>0.05) in the administration group (group G2) compared with the negative control group (IgG1m3, i.v., 0.01 mg/kg, group G1). The trend of body weight change at each time point in each group was shown in FIG. 9. The bispecific antibody CD3ExBCMA significantly inhibited tumor growth at a dose of 0.01 mg/kg with TGI (%) of 61.17%. Tumor growth was shown in FIG. 10.

Example 13: GR1803 Characterization

GR1803 is a novel recombinant humanized anti-CD3/BCMA bispecific monoclonal antibody with common light chains developed based on the Knob into Hole (KIH) technology platform. There are two identical kappa light chains with 214 amino acid residues in each, with a theoretical molecular weight of 23.4 kDa. There are two asymmetric IgG1 heavy chains of different sequences. The Knob structure targets CD3 antigen (also referred to as anti-CD3) and has 445 amino acid residues and a theoretical molecular weight of 50.5 kDa. The hole structure targets BCMA antigen (also referred to as anti-BCMA) and has 448 amino acids and a theoretical molecular weight of 50.4 kDA. In the intact molecule, there are 2 N-glycosylation sites, located at $N_{295}$ position of the heavy chain anti-CD3 and $N_{298}$ position of the heavy chain anti-BCMA, respectively; there are 17 pairs of disulfide bonds linked in the form of IgG1. GR1803 can activate T cells by specifically binding to CD3 on the surface of T cells and BCMA on the surface of tumor cells.

The intact molecular mass of an exemplary lot of GR1803 is 147853.38 Da. The molecular mass of an exemplary lot of the deglycosylated GR1803 is 144964.67 Da. In an exemplary lot, the molecular mass the reduced light chain is 23434.546 Da. In an exemplary lot, the molecular mass of the reduced anti-CD3 heavy chain is 50532.65 Da. In an exemplary lot, the molecular mass of the reduced anti-BCMA heavy chain is 50449.05 Da. In an exemplary lot, the molecular mass of the deglycosylated anti-CD3 heavy chain is 49088.30 Da. In an exemplary lot, the molecular mass of the deglycosylated anti-BCMA heavy chain is 49004.70 Da.

Two lots of GR1803 were prepared and then characterized based on protein content (UV, isoelectric point (capillary isoelectric focusing), purity (reduced and non-reduced CD-SDS), and activity (double antigen sandwich ELISA and reporter gene method). Critical quality attributes (CQAs) and critical production parameters (CPPs) of the product, including, but not limited to, pH value, elution method, load, retention time, peak collection criteria in chromatography procedures during purification, pH value and duration of low pH inactivation process; pressure in depth filtration and virus filtration, have been preliminary determined.

Capillary isoelectric focusing (cIEF) can focus and separate protein components with different changes in samples according to their isoelectric points in a certain pH gradient electrolyte. Different protein components are focused at the pH position corresponding to their respective isoelectric points to form separated protein focused bands. By adding two markers (pI markers) with known isoelectric points to the sample and focusing at the same time, the isoelectric point of the sample to be tested can be calibrated. The pI value of the main peak is the isoelectric point of the sample.

Beckman-Coulter PA800 plus capillary electrophoresis instrument was used with neutral-coated electrophoresis capillary to analyze the isoelectric point of two lots of GR1803 drug substance. The isoelectric points of the two lots of GR1803 drug substance were both 9.0 as shown in Table 7. However, the isoelectric peak may range from 8.5 to 9.5.

TABLE 7 cIEF results of two lots of GR1803 drug substances

| Sample name | Lot number | Isoelectric point (main peak pI) |
|---|---|---|
| GR1803 drug substance | 1 | 9.0 |
| | 2 | 9.0 |

The secondary structures content of the two lots of GR1803 drug substance are: α-helix: 6.8%, β-fold (antiparallel): 48.7%~48.9%, β-fold (parallel): 4.0%, β-corner: 14.7%, irregular curl: 30.0%-30.1%.

The characteristic peak wavelengths of the second derivative UV absorption spectrum of GR1803 drug substance were 287.6 nm and 294.7 nm, and the characteristic valley wavelengths were 283.4 nm and 290.6 nm. The maximum emission wavelengths of GR1803 drug substance of 280 nm excitation wavelength were 355-356 nm, and the maximum emission wavelengths at 295 nm and excitation wavelength were 353-354 nm.

The melting temperature $T_m$ of GR1803 drug substance was about 61° C., which implies good thermal stability. The pH is 4.8-5.8.

The main glycoform of GR1803 drug substance was A2G0F, with the proportion of 76.3%-77.1%; The proportion of nonfucosylated glycoform A2G0 was 2.5%; The high mannose glycoform A2G1F 2.9%-3.0%; the galactosylated glycoform A2G1F accounts for 9.8%-10.2%, A2G2F accounts for 1.4%, and A3G1F accounts for 0.5%; the other glycoforms A1G0F accounts for 2.1%-2.2%, and A3G0F accounts for 1.8%-2.0%.

The deamidation modification of GR1803 drug substance mainly occurs at the HC (anti-BCMA) $N_{316}$/HC (anti-CD3) $N_{313}$, HC (anti-BCMA) $N_{362}$, $N_{385}$, HC (anti-BCMA) $N_{390}$/HC (anti-CD3) $N_{387}$, HC (anti-BCMA) $N_{435}$/HC (anti-CD3) $N_{437}$, with the proportion of 2.2%-2.3%, 1.2%, 1.5%, 6.1%-6.2%, 2.6-2.7%, respectively.

Oxidative modification mainly occurs at LC $M_4$, HC (anti-BCMA) $M_{34}$, 162 of heavy chain, HC (anti-BCMA) $M_{253}$/HC (anti-CD3) $M_{250}$, HC (anti-BCMA) $M_{429}$, HC (anti-CD3) $M_{100}$ and 426, with the proportions of 0.1%, 0.5%-0.6%, 0.3%, 4.2%-5.1%, 0.8%-0.9%, 9.5%-11.4%, and 0.3% respectively.

HC (anti-BCMA) $D_{281}$ was isomerically modified, with the proportion of 0.1%-0.2%.

The proportion of N-terminal glutamine cyclization to pyroglutamic acid of heavy chain (anti-BCMA) was 98.2%, and that of heavy chain (anti-CD3) was 99.9%.

The proportion of non-clipped lysine at C-terminal of heavy chain was 4.6%-5.2%, and the proportion of proline amidation at C-terminal was 2.7%-3.9%.

Glycation modifications were detected at several lysine residue sites, all of which were less than 1%.

The HC (anti-BCMA) $N_{298}$/HC (anti-CD3) $N_{295}$ occurred glycosylation modification. The main gly can form was A2G0F, with the proportion of 73.0%-73.5%.

The released purity of monomer of two lots of drug substances were 99.8% and the proportion of aggregate were 0.2%. The released proportion of acidic peaks of the two lots of drug substance were 13.2% and 11.4%, the proportion of main peaks were 68.4% and 69.7%, and the proportion of basic peaks were 18.5% and 18.9%.

The release purity of IgG main peak detected of the two lots of drug substance were 94.5% and 94.4% and the proportion of fragments were 5.5% and 5.6%.

The released sum of the light chain and heavy chain contents of the two lots of drug substance was 99.4% and 94.6%, and the proportion of impurity fragments was 0.6% and 0.4%.

The proportions of pre-main peaks of peaks of the two lots of drug substances were 13.0% and 12.3%, the proportions of main peaks were 80.8% and 80.1%, and the proportions of post-major peaks were 6.2% and 7.6%.

The affinity constant KD of two lots of drug substance to CD3D & CD3E antigen were $1.261\times10^{-7}$ M and $2.412\times10^{-7}$ M.

The affinity constant KD of two lots of drug substance to BCMA-his antigen were $5.405\times10^{-10}$ M and $4.880\times10^{-10}$ M.

The two lots of drug substance can bind to FcRn under acidic conditions and the affinity constant KD were $9.243\times10^{-5}$ M and $7.917\times10^{-5}$ M. The $EC_{50}$ values of the two lots of drug substance binding to FcRn were 2.405 μg/ml and 2.455 μg/ml, respectively. Under neutral conditions, there was no obvious binding.

The GR1803 drug substance can bind to CD3D & CD3E and BCMA-his antigen simultaneously and the binding activity $EC_{50}$ values of two lots of drug substance were 8.183 μg/ml and 3.224 μg/ml, respectively.

The GR1803 drug substance can engage T cells with BCMA positive tumor cells in vitro and activate T cells. The activity $EC_{50}$ values of two lots of GR1803 drug substance were 0.045 μg/ml and 0.049 μg/ml, respectively.

After two lots of GR1803 were stored at different temperatures (≤−60° C. and −40° C.±5° C.) for 12 months, the protein content and purity basically remained unchanged, the amounts of improperly paired H and K impurity residues were all below the LOQ, and there were no significant changes in the binding activity and cell biological activity.

Sequence Listing

| SEQ ID NO | Amino Acid Sequence |
|---|---|
| 1 | GYGMH |
| 2 | VIWFDGSRKYYVDSVKG |
| 3 | QMGYWHFGL |
| 4 | RASQSISNYLT |
| 5 | EASSRPS |
| 6 | QQWSRLPVT |
| 7 | NYWMH |
| 8 | ATYRGHSDTYYNQKFKG |
| 9 | GAVYAGYDVLDY |
| 10 | QVQLVQSGAEVKKPGSSVKVSCKASGYTFTNYWMHWVRQAPGQGLEWMGATY<br>RGHSDTYYNQKFKGRVTITADKSTSTAYMELSSLRSEDTAVYYCTRGAVYAGYDV<br>LDYWGQGTTVTVSS |
| 11 | QVQLVQSGAEVKKPGSSVKVSCKASGYTFTNYWMHWVRQAPGQGLEWMGATY<br>RGHSDTYYNQKFKGRVTITADKSTSTAYMELSSLRSEDTAVYYCTRGAIYDGYDV<br>LDNWGQGTLVTVSS |
| 12 | QVQLVESGGGVVQPGRSLRLSCAASGFKFSGYGMHWVRQAPGKGLEWVAVIWFD<br>GSRKYYVDSVKGRFTISRDNSKNTLYLQMNSLRAEDTAVYYCARQMGYWHFGL<br>WGRGTLVTVSS |
| 13 | DIQMTQSPSSLSASVGDRVTITCRASQGINNSLTWYQQKPGKAPKLLIYGASNRETG<br>VPSRFSGSGSGTDFTLTISSLQPEDFATYYCQQWLKLPPTFGQGTKVEIK |
| 14 | DIQMTQSPSSLSASVGDRVTITCRASQSISNYLTWYQQKPGKAPKLLIYEASSRPSG<br>VPSRFSGSGSGTDFTLTISSLQPEDFATYYCQQWSRLPVTFGQGTKVEIK |
| 15 | ERKSCVECPPCP |
| 16 | DIQMTQSPSSLSASVGDRVTITCSASQDISNYLNWYQQKPGKAPKLLIYYTSNLHSG<br>VPSRFSGSGSGTDFTLTISSLQPEDFATYYCQQYRKLPWTFGQGTKLEIK |

-continued

Sequence Listing

| SEQ ID NO | Amino Acid Sequence |
|---|---|
| 17 | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPCP APELLGGPSVFLFPPKPKDTLMISRTPEVTCVVVDVSHEDPEVKFNWYVDGVEVHN AKTKPREEQYNSTYRVVSVLTVLHQDWLNGKEYKCKVSNKALPAPIEKTISKAKG QPREPQVYTLPPCREEMTKNQVSLWCLVKGFYPSDIAVEWESNGQPENNYKTTPP VLDSDGSFFLYSKLTVDKSRWQQGNVFSCSVMHEALHNHYTQKSLSLSPGK |
| 18 | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPCP APEFEGGPSVFLFPPKPKDTLMISRTPEVTCVVVDVSHEDPEVKFNWYVDGVEVHN AKTKPREEQYNSTYRVVSVLTVLHQDWLNGKEYKCKVSNKALPASIEKTISKAKG QPREPQVCTLPPSREEMTKNQVSLSCAVKGFYPSDIAVEWESNGQPENNYKTTPPV LDSDGSFFLVSKLTVDKSRWQQGNVFSCSVMHEALHNHYTQKSLSLSPGK |
| 19 | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPCP APEFEGGPSVFLFPPKPKDTLMISRTPEVTCVVVDVSHEDPEVKFNWYVDGVEVHN AKTKPREEQYNSTYRVVSVLTVLHQDWLNGKEYKCKVSNKALPASIEKTISKAKG QPREPQVYTLPPCREEMTKNQVSLWCLVKGFYPSDIAVEWESNGQPENNYKTTPP VLDSDGSFFLYSKLTVDKSRWQQGNVFSCSVMHEALHNHYTQKSLSLSPGK |
| 20 | RTVAAPSVFIFPPSDEQLKSGTASVVCLLNNFYPREAKVQWKVDNALQSGNSQESV TEQDSKDSTYSLSSTLTLSKADYEKHKVYACEVTHQGLSSPVTKSFNRGEC |
| 21 | GQPKAAPSVTLFPPSSEELQANKATLVCLISDFYPGAVTVAWKADSSPVKAGVETT TPSKQSNNKYAASSYLSLTPEQWKSHRSYSCQVTHEGSTVEKTVAPTECS |
| 22 | QDGNEEMGGITQTPYKVSISGTTVILTCPQYPGSEILWQHNDKNIGGDEDDKNIGSD EDHLSLKEFSELEQSGYYVCYPRGSKPEDANFYLYLRARVCENCMEMD |
| 23 | FKIPIEELEDRVFVNCNTSITWVEGTVGTLLSDITRLDLGKRILDPRGIYRCNGTDIYK DKESTVQVHYRMCQSCVELDPATVA |
| 24 | QDGNEEMGSITQTPYQVSISGTTVILTCSQHLGSEAQWQHNGKNKEDSGDRLFLPE FSEMEQSGYYVCYPRGSNPEDASHHLYLKARVCENCMEMD |
| 25 | FKIPVEELEDRVFVKCNTSVTWVEGTVGTLLTNNTRLDLGKRILDPRGIYRCNGTDI YKDKESAVQVHYRMCQNCVELDPATLA |
| 26 | DDAENIEYKVSISGTSVELTCPLDSDENLKWEKNGQELPQKHDKHLVLQDFSEVED SGYYVCYTPASNKNTYLYLKARVCEYCVEVD |
| 27 | FKIQVTEYEDKVFVTCNTSVMHLDGTVEGWFAKNKTLNLGKGVLDPRGIYLCNGT EQLAKVVSSVQVHYRMCQNCVELDSGTMA |
| 28 | MLQMAGQCSQNEYFDSLLHACIPCQLRCSSNTPPLTCQRYCNASVTNSVKGTNA |
| 29 | MLQMARQCSQNEYFDSLLHDCKPCQLRCSSTPPLTCQRYCNASMTNSVKGMN |
| 30 | MAQQCFHSEYFDSLLHACKPCHLRCSNPPATCQPYCDPSVTSSVKGTYT |
| 31 | HHHHHH |
| 32 | PRGPTIKPCPPCKCPAPNLLGGPSVFIFPPKIKDVLMISLSPIVTCVVVDVSEDDPDVQ ISWFVNNVEVHTAQTQTHREDYNSTLRVVSALPIQHQDWMSGKEFKCKVNNKDLP APIERTISKPKGSVRAPQVYVLPPPEEEMTKKQVTLTCMVTDFMPEDIYVEWTNNG KTELNYKNTEPVLDSDGSYFMYSKLRVEKKNWVERNSYSCSVVHEGLHNHHTTK SFSRTPGK |
| 33 | EPKSSDKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCKVSNK ALPAPIEKTISKAKGQPREPQVYTLPPCREEMTKNQVSLWCLVKGFYPSDIAVEWE SNGQPENNYKTTPPVLDSDGSFFLYSKLTVDKSRWQQGNVFSCSVMHEALHNHYT QKSLSLSPGK |
| 34 | EPKSSDKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCKVSNK ALPAPIEKTISKAKGQPREPQVCTLPPSREEMTKNQVSLSCAVKGFYPSDIAVEWES NGQPENNYKTTPPVLDSDGSFFLVSKLTVDKSRWQQGNVFSCSVMHEALHNHYTQ KSLSLSPGK |
| 35 | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPCP APELLGGPSVFLFPPKPKDTLMISRTPEVTCVVVDVSHEDPEVKFNWYVDGVEVHN AKTKPREEQYNSTYRVVSVLTVLHQDWLNGKEYKCKVSNKALPAPIEKTISKAKG |

-continued

| Sequence Listing | |
|---|---|
| SEQ ID NO | Amino Acid Sequence |
| | QPREPQVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGK |
| 36 | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVEPKSCDKTHTCPPCP APELLGGPSVFLFPPKPKDTLMISRTPEVTCVVVDVSHEDPEVKFNWYVDGVEVHN AKTKPREEQYNSTYRVVSVLTVLHQDWLNGKEYKCKVSNKALPAPIEKTISKAKG QPREPQVCTLPPSREEMTKNQVSLSCAVKGFYPSDIAVEWESNGQPENNYKTTPPV LDSDGSFFLVSKLTVDKSRWQQGNVFSCSVMHEALHNHYTQKSLSLSPGK |
| 37 | ASTKGPSVFPLAPSSKSTSGGTAALGCLVKDYFPEPVTVSWNSGALTSGVHTFPAV LQSSGLYSLSSVVTVPSSSLGTQTYICNVNHKPSNTKVDKRVERKSCVECPPCPAPE FEGGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPASIEKTISKAKGQP REPQVYTLPPCREEMTKNQVSLWCLVKGFYPSDIAVEWESNGQPENNYKTTPPVL DSDGSFFLYSKLTVDKSRWQQGNVFSCSVMHEALHNHYTQKSLSLSPGK |
| 38 | ASTKGPSVFPLAPSSKSTSEGTAALGCLVKDYFPEPVTVSWNSGALTSGVHTFPAVL QSSGLYSLSSVVTVPSSSLGTQTYICNVDHKPSNTKVDKTVERKSCVECPPCPAPEF EGGPSVFLFPPKPKDTLMISRTPEVTCVVVDVSQEDPEVQFNWYVDGVEVHNAKT KPREEQYNSTYRVVSVLTVLHQDWLNGKEYKCKVSNKALPASIEKTISKAKGQPR EPQVCTLPPSQEEMTKNQVSLSCAVKGFYPSDIAVEWESNGQPENNYKTTPPVLDS DGSFFLVSKLTVDKSRWQEGNVFSCSVMHEALHNHYTQKSLSLSPGK |
| 39 | QVQLVESGGGVVQPGRSLRLSCAASGFKFSGYGMHWVRQAPGKGLEWVAVIWFD GSRKYYVDSVKGRFTISRDNSKNTLYLQMNSLRAEDTAVYYCARQMGYWHFGL WGRGTLVTVSSASTKGPSVFPLAPSSKSTSGGTAALGCLVKDYFPEPVTVSWNSGA LTSGVHTFPAVLQSSGLYSLSSVVTVPSSSLGTQTYICNVNHKPSNTKVDKRVERKS CVECPPCPAPEFEGGPSVFLFPPKPKDTLMISRTPEVTCVVVDVSHEDPEVKFNWYV DGVEVHNAKTKPREEQYNSTYRVVSVLTVLHQDWLNGKEYKCKVSNKALPASIE KTISKAKGQPREPQVYTLPPCREEMTKNQVSLWCLVKGFYPSDIAVEWESNGQPEN NYKTTPPVLDSDGSFFLYSKLTVDKSRWQQGNVFSCSVMHEALHNHYTQKSLSLS PGK |
| 40 | QVQLVQSGAEVKKPGSSVKVSCKASGYTFTNYWMHWVRQAPGQGLEWMGATY RGHSDTYYNQKFKGRVTITADKSTSTAYMELSSLRSEDTAVYYCTRGAVYAGYDV LDYWGQGTTVTVSSASTKGPSVFPLAPSSKSTSEGTAALGCLVKDYFPEPVTVSWN SGALTSGVHTFPAVLQSSGLYSLSSVVTVPSSSLGTQTYICNVDHKPSNTKVDKTVE RKSCVECPPCPAPEFEGGPSVFLFPPKPKDTLMISRTPEVTCVVVDVSQEDPEVQFN WYVDGVEVHNAKTKPREEQYNSTYRVVSVLTVLHQDWLNGKEYKCKVSNKALP ASIEKTISKAKGQPREPQVCTLPPSQEEMTKNQVSLSCAVKGFYPSDIAVEWESNGQ PENNYKTTPPVLDSDGSFFLVSKLTVDKSRWQEGNVFSCSVMHEALHNHYTQKSL SLSPGK |
| 41 | DIQMTQSPSSLSASVGDRVTITCRASQSISNYLTWYQQKPGKAPKLLIYEASSRPSG VPSRFSGSGSGTDFTLTISSLQPEDFATYYCQQWSRLPVTFGQGTKVEIKRTVAAPS VFIFPPSDEQLKSGTASVVCLLNNFYPREAKVQWKVDNALQSGNSQESVTEQDSKD STYSLSSTLTLSKADYEKHKVYACEVTHQGLSSPVTKSFNRGEC |
| 42 | QVQLVESGGGVVQPGRSLRLSCAASGFKFSGYGMHWVRQAPGKGLEWVAVIWFD GSRKYYVDSVKGRFTISRDNSKNTLYLQMNSLRAEDTAVYYCARQMGYWHFGL WGRGTLVTVSSASTKGPSVFPLAPSSKSTSGGTAALGCLVKDYFPEPVTVSWNSGA LTSGVHTFPAVLQSSGLYSLSSVVTVPSSSLGTQTYICNVNHKPSNTKVDKRVEPKS CDKTHTCPPCPAPEFEGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALP ASIEKTISKAKGQPREPQVYTLPPCREEMTKNQVSLWCLVKGFYPSDIAVEWESNG QPENNYKTTPPVLDSDGSFFLYSKLTVDKSRWQQGNVFSCSVMHEALHNHYTQKS LSLSPGK |
| 43 | QVQLVQSGAEVKKPGSSVKVSCKASGYTFTNYWMHWVRQAPGQGLEWMGATY RGHSDTYYNQKFKGRVTITADKSTSTAYMELSSLRSEDTAVYYCTRGAVYAGYDV LDYWGQGTTVTVSSASTKGPSVFPLAPSSKSTSGGTAALGCLVKDYFPEPVTVSWN SGALTSGVHTFPAVLQSSGLYSLSSVVTVPSSSLGTQTYICNVNHKPSNTKVDKRVE PKSCDKTHTCPPCPAPEFEGGPSVFLFPPKPKDTLMISRTPEVTCVVVDVSHEDPEV KFNWYVDGVEVHNAKTKPREEQYNSTYRVVSVLTVLHQDWLNGKEYKCKVSNK ALPASIEKTISKAKGQPREPQVCTLPPSREEMTKNQVSLSCAVKGFYPSDIAVEWES NGQPENNYKTTPPVLDSDGSFFLVSKLTVDKSRWQQGNVFSCSVMHEALHNHYTQ KSLSLSPGK |

Sequence Description

SEQ ID NO: 1 shows the amino acid sequence of HCDR1 of the heavy chain variable region H10B7 of the anti-human CD3E monoclonal antibody H10B7+L1G10.

SEQ ID NO:2 shows the amino acid sequence of HCDR2 of the heavy chain variable region H10B7 of the anti-human CD3E monoclonal antibody H10B7+L1G10.

SEQ ID NO:3 shows the amino acid sequence of HCDR3 of the heavy chain variable region H10B7 of the anti-human CD3E monoclonal antibody H10B7+L1G10.

SEQ ID NO:4 shows the amino acid sequence of LCDR1 of the light chain variable region L9B9.

SEQ ID NO:5 shows the amino acid sequence of LCDR2 of the light chain variable region L9B9.

SEQ ID NO:6 shows the amino acid sequence of LCDR3 of the light chain variable region L9B9.

SEQ ID NO:7 shows the amino acid sequence of HCDR1 of the heavy chain variable region mutant H13F1 of the anti-human BCMA monoclonal antibody C4.

SEQ ID NO:8 shows the amino acid sequence of HCDR2 of the heavy chain variable region mutant H13F1 of the anti-human BCMA monoclonal antibody C4.

SEQ ID NO:9 shows the amino acid sequence of HCDR3 of the heavy chain variable region mutant H13F1 of the anti-human BCMA monoclonal antibody C4.

SEQ ID NO:10 shows the amino acid sequence of the heavy chain variable region mutant H13F1 of the anti-human BCMA monoclonal antibody C4.

SEQ ID NO:11 shows the amino acid sequence of the heavy chain variable region C4VH of the anti-human BCMA monoclonal antibody C4.

SEQ ID NO:12 shows the amino acid sequence of the heavy chain variable region H10B7 of the anti-human CD3E monoclonal antibody H10B7+L1G10.

SEQ ID NO:13 shows the amino acid sequence of the light chain variable region L1 G10 of the anti-human CD3E monoclonal antibody H10B7+L1G10.

SEQ ID NO:14 shows the amino acid sequence of the light chain variable region L9B9.

SEQ ID NO:15 shows the amino acid sequence of the hinge region.

SEQ ID NO:16 shows the amino acid sequence of the light chain variable region C4VK of the anti-human BCMA monoclonal antibody C4.

SEQ ID NO: 17 shows the amino acid sequence of the heavy chain constant region mutant IgG1K of human IgG1 subtype antibody.

SEQ ID NO: 18 shows the amino acid sequence of the heavy chain constant region mutant IgG1m3-H of human IgG1 subtype antibody.

SEQ ID NO:19 shows the amino acid sequence of the heavy chain constant region mutant IgG1m3-K of human IgG1 subtype antibody.

SEQ ID NO:20 shows the amino acid sequence of the light chain constant region of human kappa (x) subtype.

SEQ ID NO:21 shows the amino acid sequence of the light chain constant region of human lambda (X) subtype.

SEQ ID NO:22 shows the amino acid sequence of the extracellular region of human CD3E.

SEQ ID NO:23 shows the amino acid sequence of the extracellular region of human CD3D.

SEQ ID NO:24 shows the amino acid sequence of the extracellular region of monkey CD3E.

SEQ ID NO:25 shows the amino acid sequence of the extracellular region of monkey CD3D.

SEQ ID NO:26 shows the amino acid sequence of the extracellular region of mouse CD3E.

SEQ ID NO:27 shows the amino acid sequence of the extracellular region of mouse CD3D.

SEQ ID NO:28 shows the amino acid sequence of the extracellular region of human BCMA.

SEQ ID NO:29 shows the amino acid sequence of the extracellular region of monkey BCMA.

SEQ ID NO:30 shows the amino acid sequence of the extracellular region of mouse BCMA.

SEQ ID NO:31 shows the amino acid sequence of His tag.

SEQ ID NO:32 shows the amino acid sequence of Fc segment of mouse antibody IgG2a (mFc). SEQ ID NO:33 shows the amino acid sequence of the Fc mutant FcK of human IgG1 subtype of heterodimer.

SEQ ID NO:34 shows the amino acid sequence of the Fc mutant FcH of human IgG1 subtype of heterodimer.

SEQ ID NO: 35 shows the amino acid sequence of the heavy chain constant region of human IgG1 subtype antibody.

SEQ ID NO:36 shows the amino acid sequence of the heavy chain constant region mutant IgG1H of human IgG1 subtype antibody.

SEQ ID NO:37 shows the amino acid sequence of CD3 heavy chain constant region for GR1803.

SEQ ID NO:38 shows the amino acid sequence of BCMA heavy chain constant region for GR1803.

SEQ ID NO:39 shows the amino acid sequence of CD3 heavy chain variable region and heavy chain constant region for GR1803.

SEQ ID NO:40 shows the amino acid sequence of BCMA heavy chain variable region and heavy chain constant region for GR1803.

SEQ ID NO:41 shows the amino acid sequence of light chain variable region and light chain constant region for GR1803.

SEQ ID NO:42 shows the amino acid sequence of CD3 heavy chain variable region and heavy chain constant region for an exemplary bispecific antibody.

SEQ ID NO:43 shows the amino acid sequence of BCMA heavy chain variable region and heavy chain constant region for an exemplary bispecific antibody.

Although the present application has been described in detail with reference to the general description and specific embodiments, it will be apparent to those skilled in the art that modifications or improvements can be made to the present invention on the basis of the present application. Accordingly, all these modifications or improvements made without departing from the spirit of the present application will fall within the scope of the invention as claimed.

The invention claimed is:

1. A method of treating multiple myeloma comprising administering a bispecific antibody comprising an antigen-binding portion against human CD3 epsilon (CD3E) and an antigen-binding portion against human B-cell maturation antigen (BCMA), wherein the antigen-binding portion against human CD3E comprises:

the HCDR1 as set forth in SEQ ID NO: 1, the HCDR2 as set forth in SEQ ID NO: 2, the HCDR3 as set forth in SEQ ID NO: 3, the LCDR1 as set forth in SEQ ID NO: 4, the LCDR2 as set forth in SEQ ID NO: 5, and the LCDR3 as set forth in SEQ ID NO: 6;

and the antigen-binding portion against human BCMA comprises:

the HCDR1 as set forth in SEQ ID NO: 7, the HCDR2 as set forth in SEQ ID NO: 8, the HCDR3 as set forth in SEQ ID NO: 9, the LCDR1 as set forth in SEQ ID NO: 4, the LCDR2 as set forth in SEQ ID NO: 5, and the LCDR3 as set forth in SEQ ID NO: 6;

wherein the HCDRs and the LCDRs are defined according to Kabat, to a subject in need thereof.

* * * * *

SEQUENCE LISTING

```
Sequence total quantity: 43
SEQ ID NO: 1            moltype = AA  length = 5
FEATURE                 Location/Qualifiers
source                  1..5
                        mol_type = protein
```

```
                        organism = synthetic construct
SEQUENCE: 1
GYGMH                                                           5

SEQ ID NO: 2            moltype = AA  length = 17
FEATURE                 Location/Qualifiers
source                  1..17
                        mol_type = protein
                        organism = synthetic construct
SEQUENCE: 2
VIWFDGSRKY YVDSVKG                                              17

SEQ ID NO: 3            moltype = AA  length = 9
FEATURE                 Location/Qualifiers
source                  1..9
                        mol_type = protein
                        organism = synthetic construct
SEQUENCE: 3
QMGYWHFGL                                                       9

SEQ ID NO: 4            moltype = AA  length = 11
FEATURE                 Location/Qualifiers
source                  1..11
                        mol_type = protein
                        organism = synthetic construct
SEQUENCE: 4
RASQSISNYL T                                                    11

SEQ ID NO: 5            moltype = AA  length = 7
FEATURE                 Location/Qualifiers
source                  1..7
                        mol_type = protein
                        organism = synthetic construct
SEQUENCE: 5
EASSRPS                                                         7

SEQ ID NO: 6            moltype = AA  length = 9
FEATURE                 Location/Qualifiers
source                  1..9
                        mol_type = protein
                        organism = synthetic construct
SEQUENCE: 6
QQWSRLPVT                                                       9

SEQ ID NO: 7            moltype = AA  length = 5
FEATURE                 Location/Qualifiers
source                  1..5
                        mol_type = protein
                        organism = synthetic construct
SEQUENCE: 7
NYWMH                                                           5

SEQ ID NO: 8            moltype = AA  length = 17
FEATURE                 Location/Qualifiers
source                  1..17
                        mol_type = protein
                        organism = synthetic construct
SEQUENCE: 8
ATYRGHSDTY YNQKFKG                                              17

SEQ ID NO: 9            moltype = AA  length = 12
FEATURE                 Location/Qualifiers
source                  1..12
                        mol_type = protein
                        organism = synthetic construct
SEQUENCE: 9
GAVYAGYDVL DY                                                   12

SEQ ID NO: 10           moltype = AA  length = 121
FEATURE                 Location/Qualifiers
source                  1..121
                        mol_type = protein
                        organism = synthetic construct
SEQUENCE: 10
QVQLVQSGAE VKKPGSSVKV SCKASGYTFT NYWMHWVRQA PGQGLEWMGA TYRGHSDTYY  60
NQKFKGRVTI TADKSTSTAY MELSSLRSED TAVYYCTRGA VYAGYDVLDY WGQGTTVTVS  120
S                                                                  121

SEQ ID NO: 11           moltype = AA  length = 121
```

```
FEATURE                Location/Qualifiers
source                 1..121
                       mol_type = protein
                       organism = synthetic construct
SEQUENCE: 11
QVQLVQSGAE VKKPGSSVKV SCKASGYTFT NYWMHWVRQA PGQGLEWMGA TYRGHSDTYY  60
NQKFKGRVTI TADKSTSTAY MELSSLRSED TAVYYCTRGA IYDGYDVLDN WGQGTLVTVS  120
S                                                                 121

SEQ ID NO: 12          moltype = AA  length = 118
FEATURE                Location/Qualifiers
source                 1..118
                       mol_type = protein
                       organism = synthetic construct
SEQUENCE: 12
QVQLVESGGG VVQPGRSLRL SCAASGFKFS GYGMHWVRQA PGKGLEWVAV IWFDGSRKYY  60
VDSVKGRFTI SRDNSKNTLY LQMNSLRAED TAVYYCARQM GYWHFGLWGR GTLVTVSS    118

SEQ ID NO: 13          moltype = AA  length = 107
FEATURE                Location/Qualifiers
source                 1..107
                       mol_type = protein
                       organism = synthetic construct
SEQUENCE: 13
DIQMTQSPSS LSASVGDRVT ITCRASQGIN NSLTWYQQKP GKAPKLLIYG ASNRETGVPS  60
RFSGSGSGTD FTLTISSLQP EDFATYYCQQ WLKLPPTFGQ GTKVEIK               107

SEQ ID NO: 14          moltype = AA  length = 107
FEATURE                Location/Qualifiers
source                 1..107
                       mol_type = protein
                       organism = synthetic construct
SEQUENCE: 14
DIQMTQSPSS LSASVGDRVT ITCRASQSIS NYLTWYQQKP GKAPKLLIYE ASSRPSGVPS  60
RFSGSGSGTD FTLTISSLQP EDFATYYCQQ WSRLPVTFGQ GTKVEIK               107

SEQ ID NO: 15          moltype = AA  length = 12
FEATURE                Location/Qualifiers
source                 1..12
                       mol_type = protein
                       organism = synthetic construct
SEQUENCE: 15
ERKSCVECPP CP                                                     12

SEQ ID NO: 16          moltype = AA  length = 107
FEATURE                Location/Qualifiers
source                 1..107
                       mol_type = protein
                       organism = synthetic construct
SEQUENCE: 16
DIQMTQSPSS LSASVGDRVT ITCSASQDIS NYLNWYQQKP GKAPKLLIYY TSNLHSGVPS  60
RFSGSGSGTD FTLTISSLQP EDFATYYCQQ YRKLPWTFGQ GTKLEIK               107

SEQ ID NO: 17          moltype = AA  length = 330
FEATURE                Location/Qualifiers
source                 1..330
                       mol_type = protein
                       organism = synthetic construct
SEQUENCE: 17
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPCREE  240
MTKNQVSLWC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 18          moltype = AA  length = 330
FEATURE                Location/Qualifiers
source                 1..330
                       mol_type = protein
                       organism = synthetic construct
SEQUENCE: 18
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPEFEGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPASIEKTIS KAKGQPREPQ VCTLPPSREE  240
MTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                  330
```

```
SEQ ID NO: 19          moltype = AA  length = 330
FEATURE                Location/Qualifiers
source                 1..330
                       mol_type = protein
                       organism = synthetic construct
SEQUENCE: 19
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPEFEGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPASIEKTIS KAKGQPREPQ VYTLPPCREE  240
MTKNQVSLWC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 20          moltype = AA  length = 107
FEATURE                Location/Qualifiers
source                 1..107
                       mol_type = protein
                       organism = Homo sapiens
SEQUENCE: 20
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                107

SEQ ID NO: 21          moltype = AA  length = 106
FEATURE                Location/Qualifiers
source                 1..106
                       mol_type = protein
                       organism = Homo sapiens
SEQUENCE: 21
GQPKAAPSVT LFPPSSEELQ ANKATLVCLI SDFYPGAVTV AWKADSSPVK AGVETTTPSK  60
QSNNKYAASS YLSLTPEQWK SHRSYSCQVT HEGSTVEKTV APTECS                 106

SEQ ID NO: 22          moltype = AA  length = 105
FEATURE                Location/Qualifiers
source                 1..105
                       mol_type = protein
                       organism = Homo sapiens
SEQUENCE: 22
QDGNEEMGGI TQTPYKVSIS GTTVILTCPQ YPGSEILWQH NDKNIGGDED DKNIGSDEDH  60
LSLKEFSELE QSGYYVCYPR GSKPEDANFY LYLRARVCEN CMEMD                  105

SEQ ID NO: 23          moltype = AA  length = 84
FEATURE                Location/Qualifiers
source                 1..84
                       mol_type = protein
                       organism = Homo sapiens
SEQUENCE: 23
FKIPIEELED RVFVNCNTSI TWVEGTVGTL LSDITRLDLG KRILDPRGIY RCNGTDIYKD  60
KESTVQVHYR MCQSCVELDP ATVA                                         84

SEQ ID NO: 24          moltype = AA  length = 96
FEATURE                Location/Qualifiers
source                 1..96
                       mol_type = protein
                       organism = Macaca fascicularis
SEQUENCE: 24
QDGNEEMGSI TQTPYQVSIS GTTVILTCSQ HLGSEAQWQH NGKNKEDSGD RLFLPEFSEM  60
EQSGYYVCYP RGSNPEDASH HLYLKARVCE NCMEMD                            96

SEQ ID NO: 25          moltype = AA  length = 84
FEATURE                Location/Qualifiers
source                 1..84
                       mol_type = protein
                       organism = Macaca fascicularis
SEQUENCE: 25
FKIPVEELED RVFVKCNTSV TWVEGTVGTL LTNNTRLDLG KRILDPRGIY RCNGTDIYKD  60
KESAVQVHYR MCQNCVELDP ATLA                                         84

SEQ ID NO: 26          moltype = AA  length = 87
FEATURE                Location/Qualifiers
source                 1..87
                       mol_type = protein
                       organism = Mus musculus
SEQUENCE: 26
DDAENIEYKV SISGTSVELT CPLDSDENLK WEKNGQELPQ KHDKHLVLQD FSEVEDSGYY  60
VCYTPASNKN TYLYLKARVC EYCVEVD                                      87

SEQ ID NO: 27          moltype = AA  length = 84
FEATURE                Location/Qualifiers
source                 1..84
```

```
                        mol_type = protein
                        organism = Mus musculus
SEQUENCE: 27
FKIQVTEYED KVFVTCNTSV MHLDGTVEGW FAKNKTLNLG KGVLDPRGIY LCNGTEQLAK  60
VVSSVQVHYR MCQNCVELDS GTMA                                        84

SEQ ID NO: 28           moltype = AA  length = 54
FEATURE                 Location/Qualifiers
source                  1..54
                        mol_type = protein
                        organism = Homo sapiens
SEQUENCE: 28
MLQMAGQCSQ NEYFDSLLHA CIPCQLRCSS NTPPLTCQRY CNASVTNSVK GTNA        54

SEQ ID NO: 29           moltype = AA  length = 52
FEATURE                 Location/Qualifiers
source                  1..52
                        mol_type = protein
                        organism = Macaca fascicularis
SEQUENCE: 29
MLQMARQCSQ NEYFDSLLHD CKPCQLRCSS TPPLTCQRYC NASMTNSVKG MN          52

SEQ ID NO: 30           moltype = AA  length = 49
FEATURE                 Location/Qualifiers
source                  1..49
                        mol_type = protein
                        organism = Mus musculus
SEQUENCE: 30
MAQQCFHSEY FDSLLHACKP CHLRCSNPPA TCQPYCDPSV TSSVKGTYT             49

SEQ ID NO: 31           moltype = AA  length = 6
FEATURE                 Location/Qualifiers
source                  1..6
                        mol_type = protein
                        organism = synthetic construct
SEQUENCE: 31
HHHHHH                                                            6

SEQ ID NO: 32           moltype = AA  length = 232
FEATURE                 Location/Qualifiers
source                  1..232
                        mol_type = protein
                        organism = Mus musculus
SEQUENCE: 32
PRGPTIKPCP PCKCPAPNLL GGPSVFIFPP KIKDVLMISL SPIVTCVVVD VSEDDPDVQI  60
SWFVNNVEVH TAQTQTHRED YNSTLRVVSA LPIQHQDWMS GKEFKCKVNN KDLPAPIERT  120
ISKPKGSVRA PQVYVLPPPE EEMTKKQVTL TCMVTDFMPE DIYVEWTNNG KTELNYKNTE  180
PVLDSDGSYF MYSKLRVEKK NWVERNSYSC SVVHEGLHNH HTTKSFSRTP GK         232

SEQ ID NO: 33           moltype = AA  length = 232
FEATURE                 Location/Qualifiers
source                  1..232
                        mol_type = protein
                        organism = synthetic construct
SEQUENCE: 33
EPKSSDKTHT CPPCPAPELL GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPCR EEMTKNQVSL WCLVKGFYPS DIAVEWESNG QPENNYKTTP  180
PVLDSDGSFF LYSKLTVDKS RWQQGNVFSC SVMHEALHNH YTQKSLSLSP GK         232

SEQ ID NO: 34           moltype = AA  length = 232
FEATURE                 Location/Qualifiers
source                  1..232
                        mol_type = protein
                        organism = synthetic construct
SEQUENCE: 34
EPKSSDKTHT CPPCPAPELL GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVCTLPPSR EEMTKNQVSL SCAVKGFYPS DIAVEWESNG QPENNYKTTP  180
PVLDSDGSFF LVSKLTVDKS RWQQGNVFSC SVMHEALHNH YTQKSLSLSP GK         232

SEQ ID NO: 35           moltype = AA  length = 330
FEATURE                 Location/Qualifiers
source                  1..330
                        mol_type = protein
                        organism = Homo sapiens
SEQUENCE: 35
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
```

-continued

```
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 36          moltype = AA  length = 330
FEATURE                Location/Qualifiers
source                 1..330
                       mol_type = protein
                       organism = synthetic construct
SEQUENCE: 36
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VCTLPPSREE  240
MTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                   330

SEQ ID NO: 37          moltype = AA  length = 327
FEATURE                Location/Qualifiers
source                 1..327
                       mol_type = protein
                       organism = synthetic construct
SEQUENCE: 37
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVER KSCVECPPCP APEFEGGPSV  120
FLFPPKPKDT LMISRTPEVT CVVVDVSHED PEVKFNWYVD GVEVHNAKTK PREEQYNSTY  180
RVVSVLTVLH QDWLNGKEYK CKVSNKALPA SIEKTISKAK GQPREPQVYT LPPCREEMTK  240
NQVSLWCLVK GFYPSDIAVE WESNGQPENN YKTTPPVLDS DGSFFLYSKL TVDKSRWQQG  300
NVFSCSVMHE ALHNHYTQKS LSLSPGK                                      327

SEQ ID NO: 38          moltype = AA  length = 327
FEATURE                Location/Qualifiers
source                 1..327
                       mol_type = protein
                       organism = synthetic construct
SEQUENCE: 38
ASTKGPSVFP LAPSSKSTSE GTAALGCLVK DYFPEPVTVS WNSGALTSGV HTFPAVLQSS  60
GLYSLSSVVT VPSSSLGTQT YICNVDHKPS NTKVDKTVER KSCVECPPCP APEFEGGPSV  120
FLFPPKPKDT LMISRTPEVT CVVVDVSQED PEVQFNWYVD GVEVHNAKTK PREEQYNSTY  180
RVVSVLTVLH QDWLNGKEYK CKVSNKALPA SIEKTISKAK GQPREPQVCT LPPSQEEMTK  240
NQVSLSCAVK GFYPSDIAVE WESNGQPENN YKTTPPVLDS DGSFFLVSKL TVDKSRWQEG  300
NVFSCSVMHE ALHNHYTQKS LSLSPGK                                      327

SEQ ID NO: 39          moltype = AA  length = 445
FEATURE                Location/Qualifiers
source                 1..445
                       mol_type = protein
                       organism = synthetic construct
SEQUENCE: 39
QVQLVESGGG VVQPGRSLRL SCAASGFKFS GYGMHWVRQA PGKGLEWVAV IWFDGSRKYY  60
VDSVKGRFTI SRDNSKNTLY LQMNSLRAED TAVYYCARQM GYWHFGLWGR GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVERKS CVECPPCPAP EFEGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPASI EKTISKAKGQ PREPQVYTLP PCREEMTKNQ  360
VSLWCLVKGF YPSDIAVEWE SNGQPENNYK TTPPVLDSDG SFFLYSKLTV DKSRWQQGNV  420
FSCSVMHEAL HNHYTQKSLS LSPGK                                        445

SEQ ID NO: 40          moltype = AA  length = 448
FEATURE                Location/Qualifiers
source                 1..448
                       mol_type = protein
                       organism = synthetic construct
SEQUENCE: 40
QVQLVQSGAE VKKPGSSVKV SCKASGYTFT NYWMHWVRQA PGQGLEWMGA TYRGHSDTYY  60
NQKFKGRVTI TADKSTSTAY MELSSLRSED TAVYYCTRGA VYAGYDVLDY WGQGTTVTVS  120
SASTKGPSVF PLAPSSKSTS EGTAALGCLV KDYFPEPVTV SWNSGALTSG VHTFPAVLQS  180
SGLYSLSSVV TVPSSSLGTQ TYICNVDHKP SNTKVDKTVE RKSCVECPPC PAPEFEGGPS  240
VFLFPPKPKD TLMISRTPEV TCVVVDVSQE DPEVQFNWYV DGVEVHNAKT KPREEQYNST  300
YRVVSVLTVL HQDWLNGKEY KCKVSNKALP ASIEKTISKA KGQPREPQVC TLPPSQEEMT  360
KNQVSLSCAV KGFYPSDIAV EWESNGQPEN NYKTTPPVLD SDGSFFLVSK LTVDKSRWQE  420
GNVFSCSVMH EALHNHYTQK SLSLSPGK                                     448

SEQ ID NO: 41          moltype = AA  length = 214
FEATURE                Location/Qualifiers
source                 1..214
                       mol_type = protein
                       organism = synthetic construct
```

-continued

```
SEQUENCE: 41
DIQMTQSPSS LSASVGDRVT ITCRASQSIS NYLTWYQQKP GKAPKLLIYE ASSRPSGVPS  60
RFSGSGSGTD FTLTISSLQP EDFATYYCQQ WSRLPVTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 42          moltype = AA  length = 448
FEATURE                Location/Qualifiers
source                 1..448
                       mol_type = protein
                       organism = synthetic construct
SEQUENCE: 42
QVQLVESGGG VVQPGRSLRL SCAASGFKFS GYGMHWVRQA PGKGLEWVAV IWFDGSRKYY  60
VDSVKGRFTI SRDNSKNTLY LQMNSLRAED TAVYYCARQM GYWHFGLWGR GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEFEGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP ASIEKTISKA KGQPREPQVY TLPPCREEMT  360
KNQVSLWCLV KGFYPSDIAV EWESNGQPEN NYKTTPPVLD SDGSFFLYSK LTVDKSRWQQ  420
GNVFSCSVMH EALHNHYTQK SLSLSPGK                                     448

SEQ ID NO: 43          moltype = AA  length = 451
FEATURE                Location/Qualifiers
source                 1..451
                       mol_type = protein
                       organism = synthetic construct
SEQUENCE: 43
QVQLVQSGAE VKKPGSSVKV SCKASGYTFT NYWMHWVRQA PGQGLEWMGA TYRGHSDTYY  60
NQKFKGRVTI TADKSTSTAY MELSSLRSED TAVYYCTRGA VYAGYDVLDY WGQGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPEFEG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPASIEKTI SKAKGQPREP QVCTLPPSRE  360
EMTKNQVSLS CAVKGFYPSD IAVEWESNGQ PENNYKTTPP VLDSDGSFFL VSKLTVDKSR  420
WQQGNVFSCS VMHEALHNHY TQKSLSLSPG K                                 451
```